(12) United States Patent
Zhou et al.

(10) Patent No.: US 10,137,154 B2
(45) Date of Patent: Nov. 27, 2018

(54) METHODS AND COMPOSITIONS FOR EXPANDING LONG-TERM HEMATOPOIETIC STEM CELL POPULATIONS

(71) Applicants: THE BOARD OF TRUSTEES OF THE UNIVERSITY OF ARKANSAS, Little Rock, AR (US); Daohong Zhou, Little Rock, AR (US); Yi Luo, Little Rock, AR (US); Lijian Shao, Little Rock, AR (US); Wei Feng, Little Rock, AR (US); Jianhui Chang, Little Rock, AR (US)

(72) Inventors: Daohong Zhou, Little Rock, AR (US); Yi Luo, Little Rock, AR (US); Lijian Shao, Little Rock, AR (US); Wei Feng, Little Rock, AR (US); Jianhui Chang, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 65 days.

(21) Appl. No.: 14/903,548

(22) PCT Filed: Jul. 14, 2014

(86) PCT No.: PCT/US2014/046498
§ 371 (c)(1),
(2) Date: Jan. 7, 2016

(87) PCT Pub. No.: WO2015/006762
PCT Pub. Date: Jan. 15, 2015

(65) Prior Publication Data
US 2016/0158288 A1 Jun. 9, 2016

Related U.S. Application Data

(60) Provisional application No. 61/845,952, filed on Jul. 12, 2013.

(51) Int. Cl.
*A61K 35/28* (2015.01)
*C12N 5/0789* (2010.01)
*A61K 35/15* (2015.01)
*A61K 35/12* (2015.01)

(52) U.S. Cl.
CPC ............ *A61K 35/28* (2013.01); *A61K 35/15* (2013.01); *C12N 5/0647* (2013.01); *A61K 2035/124* (2013.01); *C12N 2501/2304* (2013.01); *C12N 2502/1157* (2013.01)

(58) Field of Classification Search
None
See application file for complete search history.

(56) References Cited

U.S. PATENT DOCUMENTS

| | | | |
|---|---|---|---|
| 2010/0291534 A1* | 11/2010 | Higuchi | C12M 33/14 435/2 |
| 2012/0064042 A1 | 3/2012 | Hematti et al. | |
| 2012/0202291 A1* | 8/2012 | Chen | C12N 5/0606 435/456 |
| 2012/0258538 A1* | 10/2012 | Nakajima | C12N 5/0647 435/455 |

FOREIGN PATENT DOCUMENTS

WO 2015006762 A1 1/2015

OTHER PUBLICATIONS

Freytes et al. "Macrophages modulate the viability and growth of human mesenchymal stem cells", Journal of cellular biochemistry 114(1): 220-229, 2013 (Year: 2013).*
Takemura et al. "Secretory products of macrophages and their physiological functions." American Journal of Physiology-Cell 246(1) : C1-C9, 1984 (Year: 1984).*
Ehninger, A. et al., "The bone marrow stem cell niche grows up: mesenchymal stem cells and macrophages move in," J. Exp. Med., Mar. 14, 2011, pp. 421-428, vol. 208, No. 3, The Rockefeller University Press.
International Search Report and Written Opinion dated Nov. 28, 2014 from related Patent Application No. PCT/US2014/046498; 10 pgs.
Winkler, I. et al., "Bone marrow macrophages maintain hematopoietic stem cell (HSC) niches and their depletion mobilizes HSCs," Blood, Dec. 2, 2010, pp. 4815-4828, vol. 116, No. 23.

* cited by examiner

*Primary Examiner* — Emily A Cordas
(74) *Attorney, Agent, or Firm* — Polsinelli PC

(57) ABSTRACT

The invention generally features compositions and methods for expanding long term hematopoietic stem cells (HSCs) in a population of cells. In particular, the invention relates to a method of expanding long term HSCs by culturing an initial population of HSCs with macrophages that promote self-renewal of long term HSCs. The expanded cell population provides a source of cells for therapeutic treatments utilizing HSC transplantation.

3 Claims, 18 Drawing Sheets

METHODS AND COMPOSITIONS FOR EXPANDING LONG-TERM HEMATOPOIETIC STEM CELL POPULATIONS

CROSS-REFERENCE TO RELATED APPLICATIONS

This application claims the benefit of PCT Application PCT/US2014/046498, filed Jul. 14, 2014, which claims the benefit of U.S. provisional application No. 61/845,952, filed Jul. 12, 2013, each of the disclosures of which are hereby incorporated by reference in its entirety.

GOVERNMENTAL RIGHTS

This invention was made with government support under R01AI080421 awarded by the National Institute of Allergy and Infectious Disease. The government has certain rights in the invention.

FIELD OF THE INVENTION

The invention relates to compositions and methods for expanding long-term hematopoietic stem cell (HSC) populations. In particular, the invention relates to populations of cells with a substantial number of long-term HSCs and culturing methods to expand numbers of long-term HSCs in cell populations.

BACKGROUND OF THE INVENTION

HSCs are responsible for sustaining hematopoietic homeostasis and regeneration after injury for the entire lifespan of an organism through self-renewal, proliferation, differentiation, and mobilization. The mature cell contingent of adult hematopoietic tissue is continuously replenished in the lifespan of an animal, due to periodical supplies from HSCs that reside permanently in the niche. To maintain blood homeostasis, these primitive cells rely on two critical properties, namely multipotency and self-renewal. Multipotency enables differentiation into multiple lineages, while self-renewal ensures preservation of fate upon cellular division. During self-renewal division, an HSC is permitted to enter the cell cycle, while restrained from engaging in differentiation, apoptosis or senescence pathways.

HSCs are rare cells that have been identified in fetal bone marrow, fetal liver, umbilical cord blood, adult bone marrow, and peripheral blood. HSCs are capable of differentiating into each of myeloerythroid (red blood cells, granulocytes, monocytes), megakaryocyte (platelets) and lymphoid (T-cells, B-cells, and natural killer cell lineages) cells. In addition, HSCs are long-lived and are capable of producing additional stem cells (self-renewal). HSCs initially undergo differentiation and commitment to lineage restricted hematopoietic progenitor cells (HPCs), which can be assayed by their ability to form colonies in semisolid media. HPCs are restricted in their ability to undergo multilineage differentiation and have lost the ability to self-renew. HPCs eventually differentiate and mature into each of the functional elements of the blood.

HSC transplantation is the only curative therapeutic modality for a variety of hematological diseases. HSCs are also attractive target cells for delivery of genes and gene products to a recipient after transplantation. However, the potential use of HSCs has been limited due to difficulties encountered with obtaining sufficient cell quantities, particularly for adult recipients and those without a matching donor. Furthermore, transplantation of insufficient HSC quantity results in an increased risk of transplantation failure and risks of transplantation complications due to a delay in donor cell engraftment.

Extensive efforts have been invested to expand HSC populations ex vivo. HSCs have been cultured with various hematopoietic growth factors and cytokines, which usually result in the expansion of HPCs, but not HSCs. Ectopic expression of an HSC regulatory transcription factor (such as HoxB4) has been shown to lead to the expansion of HSCs ex vivo, but the safety concern of cell transformation due to gene transfection limits this technique in clinical practice. HSCs have also been co-cultured with other cell types, such as with endothelial cells, mesenchymal stem cells, or bone marrow stromal cells. While these cultures resulted in maintenance or modest expansion of mouse HSC activity, they also resulted in the exhaustion of human long-term HSCs. Further, HSCs have been cultured with small molecules, such as SR-1, which have the ability to promote HSC expansion, but the effects are relatively weak and require several weeks of culture to show an effect.

Despite such efforts to expand HSC populations, only limited success has been achieved. Compositions and methods of expanding long-term HSCs in a population of cells are needed to further medical research and provide therapeutic treatments for conditions and diseases of the hematopoietic system.

SUMMARY OF THE INVENTION

In an aspect, the present invention is directed to an isolated population of cells. The isolated population of cells comprises at least one hematopoietic stem cell (HSC) and at least one macrophage cell. The macrophage cell promotes HSC expansion.

In another aspect, the present invention is directed to a method of expanding an isolated population of HSCs. The method comprises culturing a starter cell population including HSCs, adding macrophages to the starter cell population to form an expanding HSC population, and culturing the expanding HSC population to form an expanded HSC population. The number of long term HSCs is increased in comparison to the number of long term HSCs in the starter cell population.

In still another aspect, the present invention is directed to a therapeutic composition. The therapeutic composition comprises ex vivo expanded long term HSCs. The expanded long term HSCs were co-cultured with macrophages.

In yet still another aspect, the present invention is directed to a method of preparing a therapeutic composition for transiently reconstituting hematopoiesis in a subject. The method comprises culturing a starting cell population including HSCs ex vivo in a culture comprising macrophages to expand the HSCs within the cell population and resuspending the HSCs in a pharmaceutically acceptable medium suitable for administration to a recipient subject.

In yet still another aspect, the present invention is directed to a kit comprising a starter population including HSCs, macrophages and/or secreted factors from macrophages capable of promoting HSC expansion, and a container and a kit comprising macrophages and/or secreted factors from macrophages capable of promoting HSC expansion and a container.

In another aspect, the present invention is directed to an isolated population of cells. The isolated population of cells comprises at least one hematopoietic stem cell (HSC) and at least one macrophage derived secretion factor. The macrophage-derived secretion factor promotes HSC expansion.

In still another aspect, the present invention is directed to a method of expanding an isolated population of HSCs. The method comprises culturing a starter cell population including HSCs, adding at least one macrophage-derived secretion factor to the starter cell population to form an expanding HSC population, and culturing the expanding HSC population to form an expanded HSC population. The number of long term HSCs is increased in comparison to the number of long term HSCs in the starter cell population.

In still yet another aspect, the present invention is directed to a therapeutic composition. The therapeutic composition comprises ex vivo expanded long term HSCs. The expanded long term HSCs were co-cultured with at least one macrophage-derived secretion factor.

In yet still another aspect, the present invention is directed to a method of preparing a therapeutic composition for transiently reconstituting hematopoiesis in a subject. The method comprises culturing a starting cell population including HSCs ex vivo in a culture comprising at least one macrophage-derived secretion factor to expand the HSCs within the cell population and resuspending the HSCs in a pharmaceutically acceptable medium suitable for administration to a recipient subject.

BRIEF DESCRIPTION OF THE DRAWINGS

The application file contains at least one drawing executed in color. Copies of this patent application publication with color drawing(s) will be provided by the Office upon request and payment of the necessary fee.

FIG. 1A graphically depicts the gating strategies used to isolate bone marrow Gr-1 high monocytes (Gr-$1^{hi}$ MCs) (FIG. 1A, I), Gr-$1^{low}$ monocytes (Gr-$1^{low}$ MCs) (FIG. 1B, IV), and macrophages (Mφ) (FIG. 1C, V). The number of total cells (FIG. 1D), HSC-enriched Lineage negative, Sca-1 positive, and c-kit positive (Lin$^-$Sca$1^+$ c-kit$^+$ or LSK) cells (FIG. 1E), and fold of expansion of LSK cells (FIG. 1F) present in cell cultures comparing the effect of monocytes and macrophages on the expansion of HSCs ex vivo are graphically depicted. Cells without expansion culture (Input) and cultured without macrophages (W/O Mφ) were included as controls.

FIG. 3D graphically illustrates the ex vivo expansion of 5-week Cobblestone Area Forming Cells (CAFCs) representing long term HSCs from LSK cells cultured with unpolarized (Mφ), M1 polarized (M1-Mφ), and M2 (M2-Mφ) polarized macrophages.

Further, FIG. 3E shows that the fold expansion of 5-week CACFs representing long term HSCs from LSK cells cultured with unpolarized (Mφ), M1 polarized (M1-Mφ), and M2 (M2-Mφ) polarized macrophages when compared to that of input LSK cells without expansion culture. Cells cultured without macrophages (W/O Mφ) were included as a control.

FIG. 5B), B Lymphocytes (B cells; FIG. 5C), and myeloid cells (M cells; FIG. 5D) is illustrated in FIG. 5B-D. During second transplantation, only LSK cells cultured with M2-Mφ showed enhanced engraftment ability than the freshly isolated HSC cells (FIG. 5E). The engraftment of T lymphocytes (T cells; FIG. 5F), B Lymphocytes (B cells; FIG. 5G), and myeloid cells (M cells; FIG. 5H) in the secondary transplantation recipients is illustrated in FIG. 5F-H.

DETAILED DESCRIPTION OF THE INVENTION

Figure 1A:
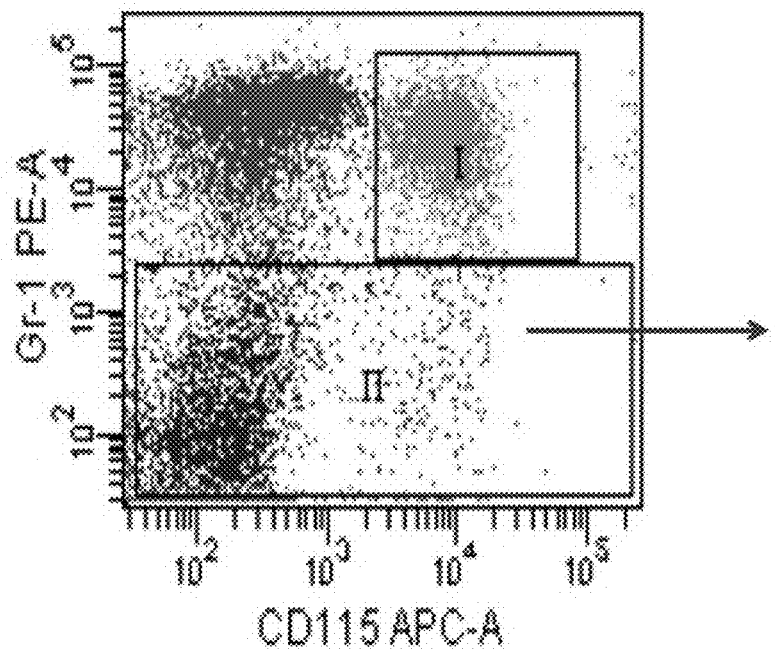
FIG. 1A, FIG. 1B, FIG. 1C, FIG. 1D, FIG. 1E and FIG. 1F show the promotion of HSC ex vivo expansion by macrophages.
Figure 1B:
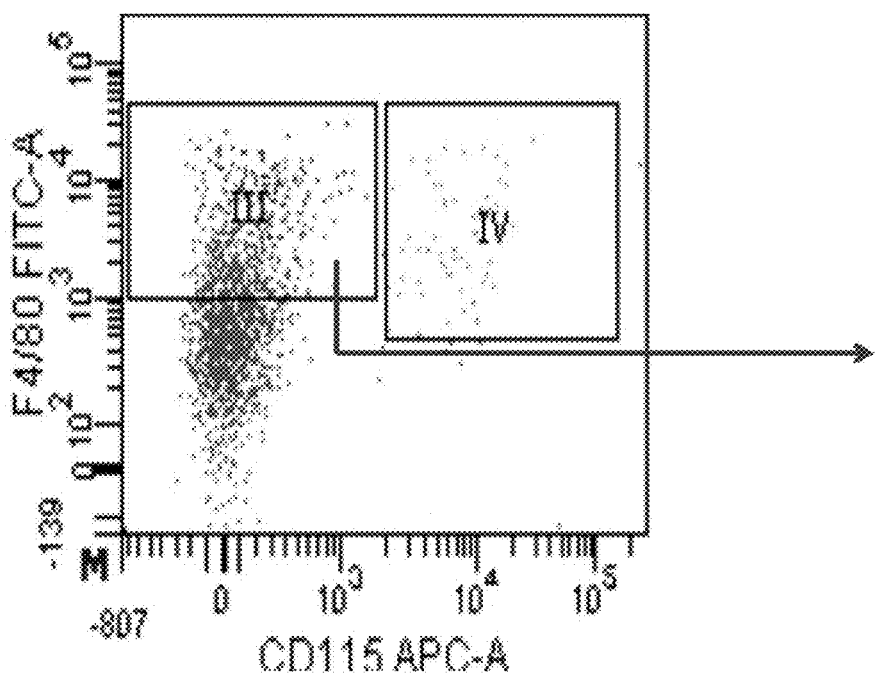
Figure 1C:
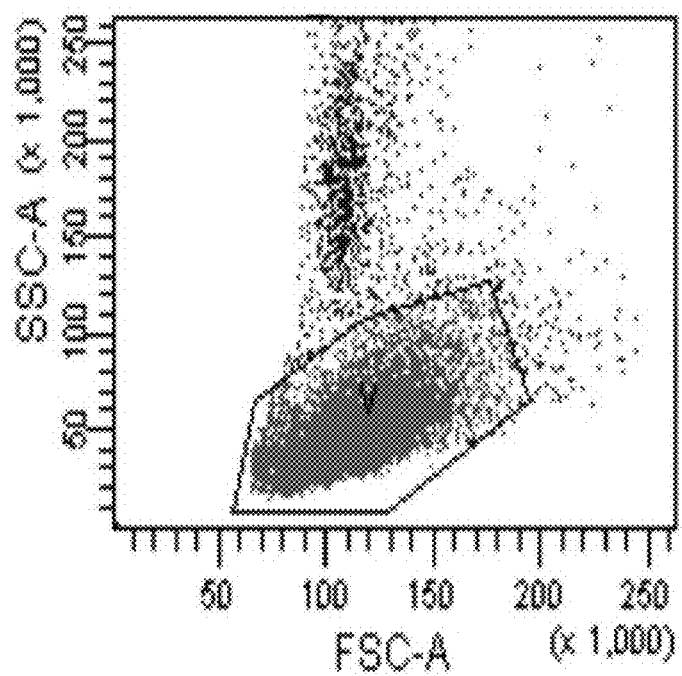
Figure 1D:
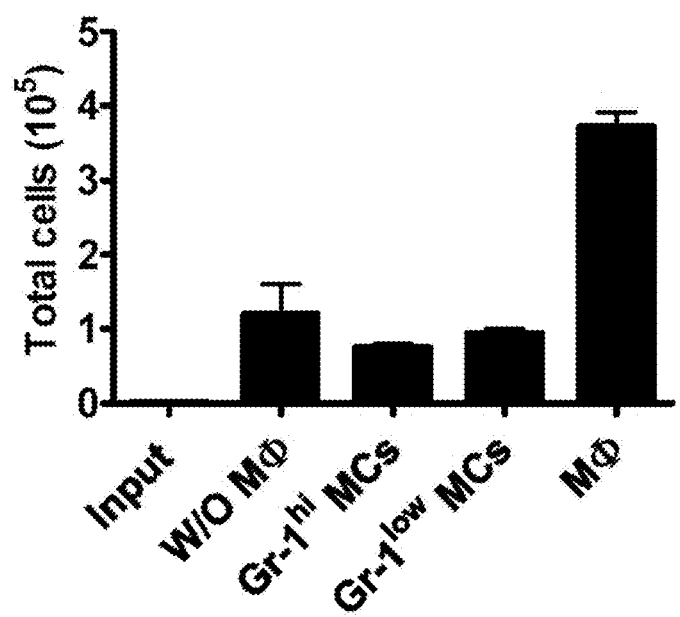
Figure 1E:
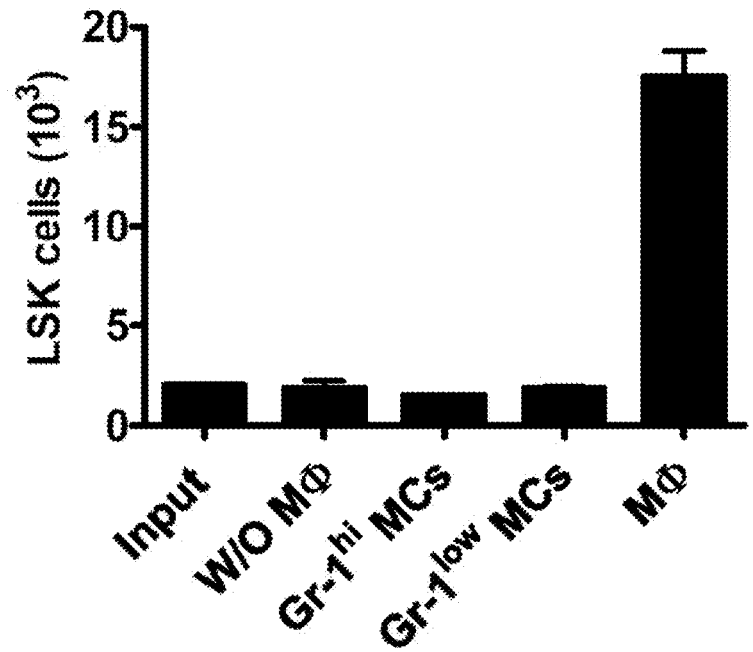

Applicants have discovered compositions and methods related to expanding the population of long-term HSCs in a cell population. In particular, the inventors have discovered that culturing HSCs in the presence of macrophages, or factors secreted by macrophages, promotes long-term HSC expansion. Such culturing methods stimulate more rapid cell cycle entry of quiescent HSCs, shorten cycling time of activated HSCs, and inhibit HSC senescence. Collectively, these effects lead to a more robust expansion of HSCs in a much shorter time than conventional methods. Accordingly, the present invention is related to compositions and methods useful in research and therapy for conditions and diseases associated with the hematopoietic system.

Various aspects of the invention are described in further detail in the following subsections.

I. Compositions

In one aspect, the present invention is directed to an isolated population of cells comprising at least one hematopoietic stem cell (HSC) and at least one macrophage cell, wherein the macrophage cell promotes HSC expansion.

In another aspect, the present invention is directed to a method of expanding an isolated population of HSCs comprising culturing a starter cell population including HSCs, adding macrophages to the starter cell population to form an expanding HSC population, and culturing the expanding HSC population to form an expanded HSC population, wherein the number of long-term HSCs is increased in comparison to the number of long-term HSCs in the starter cell population.

(a) Hematopoietic Stem Cells

The cell types relevant to the present disclosure are those of the hematopoietic system, particularly HSCs. Descriptions of cells herein will use those known to the skilled artisan, with the understanding that these descriptions reflect the current state of knowledge in the art and the invention is not limited thereby to only those phenotypic markers described herein.

HSCs are pluripotent stem cells capable of self-renewal and are characterized by their ability to give rise under permissive conditions to all cell types of the hematopoietic system. HSC self-renewal refers to the ability of an HSC cell to divide and produce at least one daughter cell with the same self-renewal ability and differentiation potential of a HSC; that is, self-renewal cell division gives rise to additional HSCs. Self-renewal provides a continual source of undifferentiated stem cells for replenishment of the hematopoietic system. HSCs are identified by their small size, lack of lineage (lin) markers, low staining (side population) with vital dyes such as rhodamine 123 (rhodamine$^{DULL}$, also called rho$^{low}$) or Hoechst 33342, and presence of various antigenic markers on their surface. The marker phenotypes useful for identifying HSCs will be those commonly known in the art. For human HSCs, the cell marker phenotypes preferably include CD34$^+$ CD38$^{low}$ CD90(Thy1)$^{low}$ Lin$^-$. In another embodiment, the cell marker for human HSCs may include: CD34$^+$ CD59$^+$ CD90 (Thy1)$^+$ CD38$^{low/-}$ c-kit(CD117)$^+$ lin$^-$. For mouse HSCs, an exemplary cell marker phenotype is Sca1$^+$ CD90$^{low}$ (see, e.g., Spangrude, G. J. et al., *Science* 1:661-673 (1988)) or Lin$^-$ Sca1$^+$ c-kit$^+$ Thy1$^{low}$ (see, Uchida, N. et al., *J. Clin. Invest.* 101(5):961-966 (1998)). In another embodiment, the cell marker for mouse HSCs may include: lin$^-$ CD34$^{low/-}$ CD150$^+$ CD135$^-$ CD48$^-$ Thy1$^{+/low}$ Sca1$^+$ c-kit$^+$. Alternative HSC markers such as aldehyde dehydrogenase (see Storms et al., *Proc. Nat'l Acad. Sci.* 96:9118-23 (1999) and AC133 (see Yin et al., *Blood* 90:5002-12 (1997)) may also find advantageous use.

HSCs may be short-term HSCs or long-term HSCs. "Short-term hematopoietic stem cell" or "ST-HSC" refers to hematopoietic stem cells that have limited, short term self-renewing capacity, and are characterized by their capacity to differentiate into cells of the myeloid and lymphoid lineage. ST-HSC are distinguished from "long-term HSCs" ("LT-HSC") by their limited length of self-renewal activity in vivo and in culture assays. LT-HSCs are capable of self-renewal. Markers may be used to distinguish long-term from short-term HSCs. In a specific embodiment, an HSC of the invention is a long-term HSC.

i. Source

Cells of the present invention may be isolated from any stem cell capable of giving rise to HSCs. Such stem cells include embryonic stem cells, adult stem cells, induced pluripotent stem cells, or cells trans-differentiated from other cell types. In an embodiment, cells may be isolated from embryonic stem cells, adult stem cells, induced pluripotent stem cells, stem cells trans-differentiated from other cell types, or combinations thereof. In a specific embodiment, cells may be isolated from adult stem cells. In another specific embodiment, cells may be isolated from embryonic stem cells. In still another specific embodiment, cells may be isolated from induced pluripotent stem cells. HSCs may be differentiated from the isolated cells. For example, HSCs may be differentiated from isolated embryonic stem cells, adult stem cells, induced pluripotent stem cells, stem cells trans-differentiated from other cell types, or combinations thereof. In a specific embodiment, HSCs may be differentiated from isolated adult stem cells. In another specific embodiment, HSCs may be differentiated from isolated embryonic stem cells. In still another specific embodiment, HSCs may be differentiated from isolated induced pluripotent stem cells.

HSCs for expansion may be obtained from a variety of sources, including bone marrow, peripheral blood, cord blood, blood, placental tissue, tissue, including liver, particularly fetal liver, other sources known to harbor HSCs, and combinations thereof. Peripheral and cord blood is a rich source of HSCs and HPCs. In a specific embodiment, HSCs may be obtained from bone marrow. In another specific embodiment, HSCs may be obtained from cord blood.

Cells are obtained using methods known and commonly practiced in the art. For example, methods for preparing bone marrow cells are described in Sutherland et al., *Bone Marrow Processing and Purging: A Practical Guide* (Gee, A P. ed.), CRC Press Inc. (1991)). Umbilical cord blood or placental cord blood is typically obtained by puncture of the umbilical vein, in both term or preterm, before or after placental detachment (see, e.g., Turner, C. W. et al., *Bone Marrow Transplant.* 10:89 (1992); Bertolini, F. et al., *J. Hematother.* 4:29 (1995)). HSCs and HPCs may also be obtained from peripheral blood by leukopheresis, a procedure in which blood drawn from a suitable subject is processed by continuous flow centrifugation to remove white blood cells while the other blood components are returned to the donor. Another type of isolation procedure is centrifugation through a medium of varying density.

The cells are derived from any animal species with a hematopoietic system, as generally described herein. Preferably, suitable animals will be mammals, including, by way of example and not limitation, rodents, rabbits, canines, felines, pigs, horses, cows, primates (e.g., human), and the like. The cells for the expansion may be obtained from a single subject, or a plurality of subjects. A plurality refers to at least two (e.g., more than one) donors. When cells obtained are from a plurality of donors, their relationships may be syngeneic, allogenenic, or xenogeneic, as defined herein. A preferred embodiment of the present disclosure is directed to a mixture of allogeneic HSCs obtained by the expansion methods herein. The allogeneic cells may be expanded separately and the cells mixed following expansion, or the cells mixed prior to expansion. In a specific embodiment, HSCs are from an allogeneic donor. In another specific embodiment HSCs are from a plurality of allogeneic donors.

Where applicable, HSCs and HPCs may be mobilized from the bone marrow into the peripheral blood by prior administration of cytokines or drugs to the subject (see, e.g., Lapidot, T. et al., *Exp. Hematol.* 30:973-981 (2002)). Cytokines and chemokines capable of inducing mobilization include, by way of example and not limitation, granulocyte colony stimulating factor (G-CSF), granulocyte macrophage colony stimulating factor (GM-CSF), erythropoietin (EPO) (Kiessinger, A et al., *Exp. Hematol.* 23:609-612 (1995)), stem cell factor (SCF), AMD3100 (AnorMed, Vancouver, Canada), interleukin-8 (IL-8), and variants of these factors (e.g., pegfilgastrim, darbopoietin). Combinations of cytokines and/or chemokines, such as G-CSF and SCF or GM-CSF and G-CSF, can act synergistically to promote mobilization and may be used to increase the number of HSCs and HPCs in the peripheral blood, particularly for subjects who do not show efficient mobilization with a single cytokine or chemokine (Morris, C. et al., *J. Haematol.* 120: 413-423 (2003)).

Cytoablative agents can be used at inducing doses (i.e., cytoreductive doses) to also mobilize HSCs, and are useful either alone or in combination with cytokines. This mode of mobilization is applicable when the subject is to undergo myeloablative treatment, and is carried out prior to the higher dose chemotherapy. Cytoreductive drugs for mobilization, include, among others, cyclophosphamide, ifosfamide, etoposide, cytosine arabinoside, and carboplatin (Montillo, M. et al., *Leukemia* 18:57-62 (2004); Dasgupta, A et al., *J. Infusional Chemother.* 6:12 (1996); Wright, D. E. et al., *Blood* 97:(8):2278-2285 (2001)).

The cells for expansion may also be subjected to further selection and purification, which may include both positive and negative selection methods, to obtain a substantially pure population of cells. In one aspect, fluorescence activated cell sorting (FACS), also referred to as flow cytometry, is used to sort and analyze the different cell populations. Cells having the cellular markers specific for HSCs or HPCs are tagged with an antibody, or typically a mixture of antibodies, that bind the cellular markers. Each antibody directed to a different marker is conjugated to a detectable molecule, particularly a fluorescent dye that can be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including by way of example and not limitation, side scatter (SSC), forward scatter (FSC), and vital dye staining (e.g., with propidium iodide) allow selection of cells based on size and viability. FACS sorting and analysis of HSCs and HPCs is described in, among others, U.S. Pat. Nos. 5,137,809, 5,750,397, 5,840,580; 6,465,249; Manz, M. G. et al., *Proc. Natl. Acad. USA* 99:11872-11877 (2002); and Akashi, K. et al., *Nature* 404(6774):193-197 (2000)). General guidance on fluorescence activated cell sorting is described in, for example, Shapiro, H. M., *Practical Flow Cytometry*, 4th Ed., Wiley-Liss (2003) and Ormerod, M. G., *Flow Cytometry: A Practical Approach,* 3rd Ed., Oxford University Press (2000).

Another method of isolating the initial cell populations uses a solid or insoluble substrate to which is bound antibodies or ligands that interact with specific cell surface markers. In immunoadsorption techniques, cells are contacted with the substrate (e.g., column of beads, flasks, magnetic particles) containing the antibodies and any unbound cells removed. Immunoadsorption techniques can be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads can be readily isolated by a magnetic separator (see, e.g., Kato, K. and Radbruch, A., *Cytometry* 14(4):38492 (1993); CD34+ direct isolation kit, Miltenyi Biotec, Bergisch, Gladbach, Germany). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations.

FACS and most batch wise immunoadsorption techniques can be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that can be employed is use of antibody/complement treatment or immunotoxins to remove unwanted cells.

It is to be understood that the purification of cells also includes combinations of the methods described above. A typical combination may comprise an initial procedure that is effective in removing the bulk of unwanted cells and cellular material, for example leukapharesis. A second step may include isolation of cells expressing a marker common to one or more of the progenitor cell populations by immunoadsorption on antibodies bound to a substrate. For example, magnetic beads containing anti-CD34 antibodies are able to bind and capture HSCs, common myeloid progenitors (CMPs), and granulocyte-monocyte progenitors (GMP) that commonly express the CD34 antigen. An additional step providing higher resolution of different cell types, such as FACS sorting with antibodies to a set of specific cellular markers, can be used to obtain substantially pure populations of the desired cells. Another combination may involve an initial separation using magnetic beads bound with anti-CD34 antibodies followed by an additional round of purification with FACS. Cells may be purified such that the starting cell population is purified HSCs. In a specific embodiment, purified HSCs are isolated $CD34^+$ cells. In another specific embodiment, purified HSCs are isolated $CD34^+$ $CD90^+$ cells. In still another specific embodiment, purified HSCs are isolated $CD34^+$ $CD90^+$ c-kit$^+$ cells. In still yet another specific embodiment, markers for purifying HSCs may be one or more markers selected from the group consisting of CD34⁺ or CD34$^{low}$, Lin⁻, CD38$^{low}$, CD90$^{low}$ or CD90⁺, CD59⁺, c-kit⁺, Sca1⁺, Thy1$^{low}$ or Thy1⁺, CD150⁺, CD135⁻, and CD48⁻. Purification of cells may result in a substantially pure population of long-term HSCs. The term "substantially pure", may be used herein to describe a purified population of HSCs that is enriched for long-term HSCs, but wherein the population of long-term HSCs are not necessarily in a pure form. Accordingly, a "substantially pure cell population" refers to a population of cells having a specified cell marker characteristic and differentiation potential that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

Determining the differentiation potential of cells, and thus the type of HSCs or HPCs isolated, is typically conducted by exposing the cells to conditions that permit development into various terminally differentiated cells. These conditions generally comprise a mixture of cytokines and growth factors in a culture medium permissive for development of the myeloid or lymphoid lineage. Colony forming culture assays rely on culturing the cells in vitro via limiting dilution and assessing the types of cells that arise from their continued development. A common assay of this type is based on methylcellulose medium supplemented with cytokines (e.g., MethoCult, Stem Cell Technologies, Vancouver, Canada; Kennedy, M. et al., *Nature* 386:488-493 (1997)). Cytokine and growth factor formulations permissive for differentiation in the hematopoietic pathway are described in Manz et al., *Proc. Natl. Acad. Sci. USA* 99(18): 11872-11877 (2002); U.S. Pat. No. 6,465,249; and Akashi, K. et al., *Nature* 404(6774):193-197 (2000)). Cytokines include SCF (stem cell factor), FLT-3 ligand, GM-CSF, IL-3, TPO (thrombopoietin), and EPO (erythropoietin). Another in vitro assay is CAFC (cobblestone area-forming cell) assay or long-term culture initiating cell (LTC-IC) assay, which typically uses stromal cells to support hematopoiesis (see, e.g., Ploemacher, R. E. et al., *Blood.* 74:2755-2763 (1989); and Sutherland, H. J. et al., *Proc. Natl. Acad. Sci. USA* 87:3745 (1995)).

Another type of assay suitable for determining the differentiation potential of isolated cells relies upon in vivo administration of cells into a host animal and assessment of the repopulation of the hematopoietic system. The recipient is immunocompromised or immunodeficient to limit rejection and permit acceptance of allogeneic or xenogeneic cell transplants. A useful animal system of this kind is the NOD/SCID mice (Pflumio, F. et al., *Blood* 88:3731 (1996); Szilvassym S. J. et al., "Hematopoietic Stem Cell Protocol," in *Methods in Molecular Medicine*, Humana Press (2002); Greiner, D. L. et al., *Stem Cells* 16(3):166-177 (1998); Piacibello, W. et al., *Blood* 93:(11):3736-3749 (1999)) or Rag2 deficient mouse (Shinkai, Y. et al., *Cell* 68:855-867 (1992)). Cells originating from the infused cells are assessed by recovering cells from the bone marrow, spleen, or blood of the host animal and determining presence of cells displaying specific cellular markers, (i.e., marker phenotyping) typically by FACS analysis. Detection of markers specific to the transplanted cells permits distinguishing between endogenous and transplanted cells. For example, antibodies specific to human forms of the cell markers (e.g., HLA antigens) identify human cells when they are transplanted into a suitable immunodeficient mouse.

The HSCs may be used directly for expansion or may be frozen for use at a later date. The HSCs may be frozen individually or together with macrophages (described below) prior to co-culturing. A variety of mediums and protocols for freezing cells are known in the art. Generally, the freezing medium comprises 5-10% dimethyl sulfoxide (DMSO), 10-50% serum, and 50-90% culture medium. Preferably, the freezing medium comprises 5-10% DMSO, 10-20% serum, and 70-85% culture medium. Other additives useful for preserving cells include, by way of example and not limitation, disaccharides such as trehalose (Scheinkonig, C. et al., *Bone Marrow Transplant.* 34(6):531-6 (2004)), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% DMSO, and 2% hetastarch. Other compositions and methods for cryopreservation are well known and described in the art (see, e.g., Broxmeyer, H. E. et al., *Proc. Natl. Acad. Sci. USA* 100(2) .645-650 (2003)). Cells are preserved at a final temperature of less than about −135° C.

(b) Macrophages

A macrophage of the present invention may be any macrophage type capable of promoting HSC self-renewal or expansion of HSCs. In a specific embodiment, a macrophage may promote expansion of long-term HSCs.

Macrophages are cells produced by the differentiation of monocytes in tissues. Macrophages undergo specific differentiation depending on the local tissue environment. Macrophages can be phenotypically polarized by the microenvironment to mount specific functional programs. Two distinct states of polarized activation for macrophages have been defined: the classically activated (M1) macrophage phenotype and the alternatively activated (M2) macrophage phenotype. Granulocyte macrophage colony stimulating factor (GM-CSF) and macrophage colony stimulating factor (M-CSF) are involved in the differentiation of monocytes to macrophages. Human GM-CSF can polarize monocytes towards the M1 macrophage subtype with a "pro-inflammatory" cytokine profile (e.g. TNF, IL-23). Whereas, treatment with M-CSF produces an "anti-inflammatory" cytokine (e.g. IL-10) profile similar to M2 macrophages. The role of the classically activated (M1) macrophage is an effector cell in $T_H1$ cellular immune responses, whereas the alternatively activated (M2) macrophage appears to be involved in immunosuppression and wound healing/tissue repair. LPS and the $T_H1$ cytokine IFN-gamma polarize macrophages towards the M1 phenotype which induces the macrophage to produce large amounts of TNF, IL-12, and IL-23. In contrast, exposure of macrophages to the $T_H2$ cytokine IL-4 produces a M2 phenotype which induces the production of high levels of IL-10 and IL-1 RA, and low expression of IL-12. M2 macrophages can be further divided into subsets: M2a, M2b, and M2c based on gene expression profiles. A third subset of activated macrophages, called regulatory macrophages or M2d macrophages, dampens immune responses by producing the immunosuppressive cytokine, IL-10. Regulatory macrophages are induced by a variety of stimuli including glucocorticoids released from adrenal cells and prostaglandins. A macrophage of the invention may be an unpolarized macrophage, a M1 polarized macrophage, a M2 polarized macrophage, or combinations thereof. In a specific embodiment, a macrophage may be a M2 polarized macrophage. A M1 polarized macrophage may be stimulated or activated by IFN-gamma, TNF-alpha, LPS, or combinations thereof. A M2 polarized macrophage may be stimulated or activated by IL-4, IL-13, ICs (immune complexes), LPS, LTR, IL-1R, IL-10, TGF-beta, GCs, IL-6, LIF (leukocyte inhibitory factor), MCF, or combinations thereof. In a specific embodiment, a M1 polarized macrophage is stimulated or activated by IFN-gamma. In another specific embodiment, a M2 polarized macrophage is stimulated or activated by IL-4. A macrophage of the invention may be polarized after isolation of the macrophage. Alternatively, a macrophage of the invention may be isolated as a polarized macrophage.

Macrophages may be found at points where microbial invasion or accumulation of foreign particles are likely to occur. Each type of macrophage, determined by its location, has a specific name. Suitable macrophages may include, but are not limited to, adipose tissue macrophages, monocytes, Kupffer cells, sinus histiocytes, alveolar macrophages, tissue macrophages, Langerhans cells, microglias, Hofbauer cells, intraglomerular mesangial cells, osteoclasts, epthelioid cells, red pulp macrophages or peritoneal macrophages. Non-limiting examples of a tissue comprising macrophages include adipose tissue, bone marrow, blood, liver, lymph node, pulmonary alveolus, connective tissue, skin, mucosa, central nervous system, placenta, kidney, bone, granuloma, spleen, or peritoneal cavity. In specific embodiments, a macrophage of the invention may be from the blood, the bone marrow, the spleen, the peritoneal cavity, or combinations thereof. In other specific embodiments, a macrophage of the invention may be a monocyte, a red pulp macrophage, a peritoneal macrophage, or combinations thereof. In an embodiment where a monocyte is from the bone marrow, macrophage colony-stimulating factor (M-CSF) may be used to differentiate the monocytes into mature macrophages. In another embodiment, macrophages may be derived from cord blood cells, peripheral blood cells, bone marrow cells, placental cells, tissue cells, embryonic stem cells, adult stem cells, inducible pluripotent stem cells, stem cells trans-differentiated from other cells, or combinations thereof. In a specific embodiment, macrophages may be derived from cord blood cells.

Macrophages may be isolated according to methods standard in the art. For example, see Zhang et al., *Curr Protoc Immunol*, 2008, CHAPTER: Unit-14.1. Additionally, macrophages may be isolated according to methods described in Section I(a). Macrophages can be identified by specific expression of a number of proteins including, but not limited to, CD14, CD40, CD11b, CD64, F4/80 (mice)/EMR1 (human), lysozyme M, MAC-1/MAC-3, CD68, CSF1R, MAC-2, CD11c, LY6C, IL-4Ra and CD163 by flow cytometry or immunohistochemical staining. Flow cytometry may be used to isolate macrophages from other hematopoietic cells. Generally, a combination of antibodies against several cell-specific antigens may be used to identify macrophages. In an embodiment, CD11b and F4/80/EMR1 may be used to isolate macrophages. In another embodiment, CD11b, F4/80/EMR1, and CD68 may be used to isolate macrophages. In still another embodiment, one or more surface markers may be used to isolate macrophages. The one or more surface markers may include, but is not limited to, CD204, CD36, CD14, CD18, CD11b, CD64, CD32, CD16, CD88, CD303, CD209, CD205, CD282, CD284, CD80 and CD86. In a specific embodiment, cord blood mononuclear cells may be isolated from which CD34⁻ cells may be further isolated. The isolated CD34⁻ cells may be differentiated to macrophages. Macrophage differentiation may occur by incubation with SCF and M-CSF.

The macrophages may be used directly for expansion or may be frozen for use at a later date. The macrophages may be frozen individually or together with HSCs prior to co-culturing. A variety of mediums and protocols for freezing cells are known in the art. Generally, the freezing medium comprises 5-10% dimethyl sulfoxide (DMSO), 10-50% serum, and 50-90% culture medium. Preferably, the freezing medium comprises 5-10% DMSO, 10-20% serum, and 70-85% culture medium. Other additives useful for preserving cells include, by way of example and not limitation, disaccharides such as trehalose (Scheinkonig, C. et al., *Bone Marrow Transplant*. 34(6):531-6 (2004)), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% DMSO, and 2% hetastarch. Other compositions and methods for cryopreservation are well known and described in the art (see, e.g., Broxmeyer, H. E. et al., *Proc. Natl. Acad. Sci. USA* 100(2).645-650 (2003)). Cells are preserved at a final temperature of less than about −135° C.

(c) Contacting

In one aspect, HSCs are co-cultured with macrophages to promote HSC expansion. In another aspect, HSCs are contacted with at least one macrophage-derived secretion factor that promotes HSC expansion. In still another aspect, HSCs may be co-cultured with macrophages and contacted with additional factors to promote HSC expansion.

HSCs, described in Section I(a), are co-cultured with macrophages, described in Section I(b). HSCs and macrophages may be co-cultured at a 1:1 ratio. Alternatively, HSCs and macrophages may be co-cultured at a ratio less than 1:1. For example, the ratio of HSCs to macrophages may be about 1:1000, about 1:500, about 1:100, about 1:50, about 1:10, or about 1:5. In a specific embodiment, the ratio of HSCs to macrophages may be about 1:50. Alternatively, HSCs and macrophages may be co-cultured at a ratio greater than 1:1. For example, the ratio of HSCs to macrophages may be about 100:1, about 50:1, about 10:1, or about 5:1.

Cells of the present invention may be contacted with additional factors to promote expansion. Such additional factors include cytokines, growth factors, polypeptides, proteins, small molecules, genes, expression vectors, nutrients, and other factors known in the art or yet to be discovered. Suitable factors may include macrophage-derived secretion factors that promote HSC expansion. Macrophage-derived secretion factors may be isolated by methods known in the art. For example, macrophage-derived secretion factors may be isolated from macrophage cultures in which the macrophages have been removed, for example by filtering or centrifugation. A skilled artisan will recognize the numerous additional factors known in the art for promoting expansion of stem cells. A preferred additional factor may be an additional factor that can stimulate HSC self-renewal proliferation and/or inhibit HSC differentiation, apoptosis and senescence. In one aspect, the cells of the present invention are contacted with no more than 10 additional factors. In another aspect, the cells of the present invention are contacted with no more than 9, 8, 7, 6, 5, 4, or 3 additional factors. In yet another aspect, the cells of the present invention are contacted with no more than 3 additional factors. In still yet another aspect, the cells of the present invention are contacted with no more than 2 additional factors. In a specific embodiment, the cells of the present invention are contacted with TPO and SCF. In another specific embodiment, the cells of the present invention are contacted with TPO, SCF and Flt-3 ligand. A skilled artisan would be able to determine the amount of additional factor to be added to promote expansion. In an embodiment, cells of the present invention may be contacted with about 10 to about 100 ng/ml of TPO, SCF and/or Flt-3 ligand. For example, cells of the present invention may be contacted with about 10, about 20, about 30, about 40, about 50, about 60, about 70, about 80, about 90, or about 100 ng/ml of TPO, SCF and Flt-3 ligand. In a specific embodiment, cells of the present invention may be contacted with 20 ng/ml of TPO and SCF. In another specific embodiment, cells of the present invention may be contacted with 50 ng/ml of TPO, SCF and Flt-3 ligand.

(d) Expanding a Population of HSCs

One aspect of the invention includes methods of expanding a population of HSCs, the methods include culturing a starter cell population including HSCs; adding macrophages to the starter cell population to form an expanding HSC population; and culturing the expanding HSC population to form an expanded HSC population, wherein the number of long term HSCs is increased in comparison to the number of long term HSCs in the starter cell population.

The starter cell population may be a population obtained as described in Section I(a). The starter cell population of cells are contacted with a basal medium and cultured to expand the population of HSCs. The basal medium may contain a mixture of additional factors such as cytokines and growth factors. The starter population may comprise additional factors as described in Section I(c). In one aspect, the basal medium includes amino acids, carbon sources (e.g., pyruvate, glucose, etc.), vitamins, serum proteins (e.g., albumin), inorganic salts, divalent cations, antibiotics, buffers, and other preferably defined components that support expansion of HSCs. Suitable basal mediums include, without limitation, RPMI medium, Iscove's medium, minimum essential medium, Dulbecco's Modified Eagles Medium, and others known in the art. The formulations of these and other mediums will be apparent to the skilled artisan.

Expansion is done for from about 1 day to about 30 days, preferably from about 5 days to about 15 days, more preferably about 7 days to about 10 days or until the indicated fold expansion. Such HSC expansion results in an increase of HSCs compared to the number of HSCs in the initial population. In certain aspects, the HSC expansion results in an increase of long-term HSCs compared to the number of long-term HSCs in the initial population. In certain aspects, the HSC expansion results in an increase of short-term HSCs compared to the number of short-term HSCs in the initial population. In certain aspects, the HSC expansion results in an increase of long- and short-term HSCs compared to the number of long- and short-term HSCs in the initial population. Preferably, there is an increase of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or more fold. In certain aspects, there is an increase of about 1.5 to 5 fold. In some aspects, there is an increase of about 1, 1.25, 1.5, 1.75, 2.0, 2.25, 2.5, 2.75, 3.0, 3.5, 4.0, 4.5, or 5.0 fold.

(e) Therapeutic Composition

Following harvest and expansion, HSCs, HPCs, or a mixture of cells that include these cells may be combined with pharmaceutical carriers/excipients known in the art to enhance preservation and maintenance of the cells prior to administration. Accordingly, the expanded HSCs may be formulated into a therapeutic composition. As such, the invention encompasses a therapeutic composition comprising ex vivo expanded HSCs, wherein the expanded HSCs were co-cultured with macrophages. In a specific embodiment, the invention encompasses a therapeutic composition comprising ex vivo expanded long-term HSCs, wherein the expanded long-term HSCs were co-cultured with macrophages.

In an aspect, a method of preparing a therapeutic composition for transiently reconstituting hematopoiesis in a subject comprises culturing a starting cell population including HSCs ex vivo in a culture comprising macrophages to expand the HSCs within the cell population and resuspending the HSCs in a pharmaceutically acceptable medium suitable for administration to a recipient subject.

Pharmaceutically acceptable mediums suitable for administration to a subject are known in the art. In some embodiments, cell compositions of the invention can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene, glycol, liquid polyethylene glycol, and the like) and suitable mixtures thereof.

Sterile injectable solutions can be prepared by incorporating the expanded HSCs of the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "Remington's Pharmaceutical Science", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, may be added. Prevention of the action of microorganisms can be ensured by various antibacterial and antifungal agents, for example, parabens, chlorobutanol, phenol, sorbic acid, and the like. The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

In another aspect, the expanded long-term HSCs are cryopreserved in a cryopreservation medium. The HSCs may be cryopreserved prior to resuspending in a pharmaceutically acceptable medium. Alternatively, the starting cell population of HSCs may be cryopreserved prior to culturing in a culture comprising macrophages. A variety of mediums and protocols for freezing cells are known in the art. Generally, the freezing medium comprises 5-10% dimethyl sulfoxide (DMSO), 10-50% serum, and 50-90% culture medium. Preferably, the freezing medium comprises 5-10% DMSO, 10-20% serum, and 70-85% culture medium. Other additives useful for preserving cells include, by way of example and not limitation, disaccharides such as trehalose (Scheinkonig, C. et al., *Bone Marrow Transplant.* 34(6): 531-6 (2004)), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% DMSO, and 2% hetastarch. Other compositions and methods for cryopreservation are well known and described in the art (see, e.g., Broxmeyer, H. E. et al., *Proc. Natl. Acad. Sci. USA* 100(2).645-650 (2003)). Cells are preserved at a final temperature of less than about −135° C.

II. Methods of Use

The methods of the present invention include methods of using the expanded HSCs for HSC based therapies. Accordingly, the methods of the invention may be used to treat a disease or disorder in which it is desirable to increase the number of HSCs or their progenitors. Frequently, subjects in need of the inventive treatment methods will be those undergoing or expecting to undergo a blood cell (e.g., an immune cell) depleting treatment, such as chemotherapy.

Thus, methods of the invention may be used, for example, to treat patients requiring a bone marrow transplant or a HSC transplant (e.g., to reconstitute the hematopoietic system/ tissue), such as cancer patients undergoing chemotherapy and/or radiation therapy. Disorders treated by methods of the invention may be the result of an undesired side effect or complication of another primary treatment, such as radiation therapy, chemotherapy, or treatment with a bone marrow suppressive drug. Methods of the invention may further be used as a means to increase the number of mature cells derived from HSCs (e.g., erythrocytes, lymphocytes). For example, disorders or diseases characterized by a lack of, or low levels of, blood cells, or a defect in blood cells, may be treated by increasing the pool of HSCs. Such conditions include, for example, pancytopenia, neutropenia, thrombocytopenia, anemia and lymphopenia. The disorder to be treated may also be the result of an infection causing damage to blood/lymphoid cells and/or stem cells.

In one aspect, the methods of the invention include administering the expanded HSCs to reconstitute the hematopoietic system or tissue of a subject. In another aspect, the methods include administering the expanded HSCs to a subject for hematopoietic stem cell transplantation. Another aspect includes administering the expanded HSCs to a subject for increasing the number of blood cells in a subject. In still another aspect, the present invention includes a method for reconstituting the hematopoietic system or tissue of a subject. Such methods include administering to a recipient subject an HSC population of the present invention.

The expanded HSCs may be administered to a subject as a mixture of HSCs and other cell types, such as HPCs and macrophages. In another aspect, the expanded HSCs may be administered to a subject as a substantially pure population of HSCs. In another aspect, the expanded HSCs may be differentiated into specific cell types and then administered to a subject.

Administered HSCs of the invention may be present in the recipient subject at 1 month or more following administration. For example, HSCs of the invention may be present at 1, 2, 3, 4, 5, 6, 7, 8, 9, 10, 11, or 12 months or more following administration. Administered HSCs may be present as donor-derived white bloods cells such as donor-derived T cells, B cells and myeloid cells. Methods of detecting the presence of donor-derived cells are known in the art and may include flow cytometry.

In another aspect, the present invention provides a use of the composition of the present invention for hematopoietic stem cell transplantation. The present invention also provides a use of the composition of the present invention for reconstituting the hematopoietic system or tissue of a subject. In still another aspect, the present invention provides a use of the composition of the present invention for the preparation of a medicament for reconstituting the hematopoietic system or tissue of a subject. The present invention also provides a use of the present invention for increasing the number of blood cells in a subject.

As used herein, "subject" or "patient" is used interchangeably. Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In specific embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In a preferred embodiment, the subject is human.

(a) Administration

HSCs, HPCs, or a mixture comprising such cell types may be administered to a subject according to methods known in the art. Such compositions may be administered by any conventional route, including injection or by gradual infusion over time. The administration may, depending on the composition being administered, for example, be, pulmonary, intravenous, intraperitoneal, intramuscular, intracavity, subcutaneous, or transdermal. The stem cells are administered in "effective amounts", or the amounts that either alone or together with further doses produce the desired therapeutic response. Administered cells of the invention may be autologous ("self") or heterologous/non-autologous ("non-self," e.g., allogeneic, syngeneic or xenogeneic). Generally, administration of the cells can occur within a short period of time following the expansion of HSCs (e.g., 1, 2, 5, 10, 24, 48 hours, 1 week or 2 weeks after the expansion)) and according to the requirements of each desired treatment regimen. For example, where radiation or chemotherapy is conducted prior to administration, treatment, and transplantation of stem cells of the invention should optimally be provided within about one month of the cessation of therapy. However, transplantation at later points after treatment has ceased may be done with derivable clinical outcomes.

The quantity of cells to be administered will vary for the subject being treated. The precise determination of what would be considered an effective dose may be based on factors individual to each patient, including their size, age, sex, weight, and condition of the particular patient. As few as 100-1000 cells may be administered for certain desired applications among selected patients. Therefore, dosages can be readily ascertained by those skilled in the art from this disclosure and the knowledge in the art. The skilled artisan can readily determine the amount of cells and optional additives, vehicles, and/or carrier in compositions and to be administered in methods of the invention.

The pharmaceutical composition of the present invention is administered in a manner compatible with the dosage formulation, and in a therapeutically effective amount, for example intravenously, intraperitoneally, intramuscularly, subcutaneously, and intradermally. It may also be administered by any of the other numerous techniques known to those of skill in the art, see for example the latest edition of Remington's Pharmaceutical Science, the entire teachings of which are incorporated herein by reference. For example, for injections, the pharmaceutical composition of the present invention may be formulated in adequate solutions including but not limited to physiologically compatible buffers such as Hank's solution, Ringer's solution, or a physiological saline buffer. The solutions may contain formulatory agents such as suspending, stabilizing, and/or dispersing agents. Alternatively, the pharmaceutical composition of the present invention may be in powder form for combination with a suitable vehicle, e.g., sterile pyrogen free water, before use. Further, the composition of the present invention may be administered per se or may be applied as an appropriate formulation together with pharmaceutically acceptable carriers, diluents, or excipients that are well known in the art. In addition, other pharmaceutical delivery systems such as liposomes and emulsions that are well known in the art, and a sustained-release system, such as semi-permeable matrices of solid polymers containing a therapeutic agent, may be employed. Various sustained-release materials have been established and are well-known to one skilled in the art. Further, the composition of the present invention can be administered alone or together with another therapy conventionally used for the treatment of a disease/condition associated with poor expansion and/or differentiation of HSCs, or in which expansion and/or differentiation of HSCs is desirable.

III. Kits

In another aspect, the disclosure provides kits containing initial cells for expansion, media and other necessary components for carrying out the ex vivo expansion methods. Kits directed to use of the cell populations, expanded or unexpanded, for therapeutic applications are provided. The kits may further include, by way of example and not limitation, buffers, labels, reagents, and instructions for methods of using the kits. In an embodiment, a kit may comprise a starter population including HSCs, macrophages and a container. In another embodiment, a kit may comprise a starter population including HSCs, secreted factors from macrophages capable of promoting HSC expansion and a container. In still another embodiment, a kit may comprise macrophages and other components needed to expand HSCs ex vivo. Other components may include secreted factors from macrophages capable of promoting HSC expansion.

Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

"Allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor.

"Autologous" refers to deriving from or originating in the same subject or patient. An "autologous transplant" refers to the harvesting and reinfusion or transplant of a subject's own cells or organs. Exclusive or supplemental use of autologous cells can eliminate or reduce many adverse effects of administration of the cells back to the host, particular graft versus host reaction.

"Chemically-defined" as used herein refers to culture media of known chemical composition, both quantitatively and qualitatively, with no deliberately added uncharacterized supplements, even though such a medium may contain trace contaminants in its components. A chemically defined medium necessarily lacks animal serum, feeder cells such as stromal cells, and cell-based extracellular matrices derived from, e.g., fibroblasts and the like.

"Cytokine" refers to compounds or compositions that in the natural state are made by cells and affect physiological states of the cells that produce the cytokine (i.e., autocrine factors) or other cells. Cytokine also encompasses any compounds or compositions made by recombinant or synthetic processes, where the products of those processes have identical or similar structure and biological activity as the naturally occurring forms. Lymphokines refer to natural, synthetic, or recombinant forms of cytokines naturally produced by lymphocytes, including, but not limited to, IL-1, IL-3, IL-4, IL-6, IL-11, and the like.

"Expansion" in the context of cells refers to increase in the number of a characteristic cell type, or cell types, from an initial population of cells, which may or may not be identical. The initial cells used for expansion need not be the same as the cells generated from expansion. For instance, the expanded cells may be produced by growth and differentiation of the initial population of cells. Excluded from the term expansion are limiting dilution assays used to characterize the differentiation potential of cells. As used herein, "expansion" and "self-renewal" are used interchangeably and refer to the propagation of a cell or cells without terminal differentiation and "differentiation" refers to the developmental process of lineage commitment. A "lineage" refers to a pathway of cellular development, in which precursor or "progenitor" cells undergo progressive physiological changes to become a specified cell type having a characteristic function (e.g., a T cell, a macrophage). Differentiation occurs in stages, whereby cells gradually become more specified until they reach full maturity.

"Growth factor" refers to a compound or composition that in the natural state affects cell proliferation, cell survival, and/or differentiation. A growth factor, while having the indicated effect on the cell, may also affect other physiological process, such as secretion, adhesion, response to external stimuli, and the like. Although many growth factors are made by cells, growth factors as used herein also encompass any compound or composition made by recombinant or synthetic processes, where the product of those processes have identical or similar structure and biological activity as the naturally occurring growth factor. Examples of growth factors include epidermal growth factor (EGF), fibroblast growth factor (FGF), erythropoietin (EPO), thrombopoietin (TPO), stem cell factor (SCF), and flt-3 ligand (FL), and analogs thereof.

"Isolated" refers to a product, compound, or composition which is separated from at least one other product, compound, or composition with which it is associated in its naturally occurring state, whether in nature or as made synthetically.

"Hematopoietic stem cell" or "HSC" refers to a clonogenic, self-renewing pluripotent cell capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers.

"Enriched" when used in the context of HSC refers to a cell population selected based on the presence of a single cell marker, generally CD34+, while "purified" in the context of HSC refers to a cell population resulting from a selection on the basis of two or more markers, preferably CD34+ CD90+.

"Myeloablative" or "myeloablation" refers to impairment or destruction of the hematopoietic system, typically by exposure to a cytotoxic agent or radiation. Myeloablation encompasses complete myeloablation brought on by high doses of cytotoxic agent or total body irradiation that destroys the hematopoietic system. It also includes a less than complete myeloablated state caused by non-myeloablative conditioning. Thus, non-myeloablative conditioning is treatment that does not completely destroy the subject's hematopoietic system.

"Sorting" as it pertains to cells refers to separation of cells based on physical characteristics (such as, e.g., elutriation or other size-based techniques) or presence of markers (such as sorting using side scatter (SSC) and forward scatter (FSC), or fluorescence activation cell sorting (FACS) using labeled antibodies), or analysis of cells based on presence of cell markers, e.g., FACS without sorting, and including as well immunoabsorption techniques such as, e.g., magnetic cell separation systems.

"Substantially pure cell population" refers to a population of cells having a specified cell marker characteristic and differentiation potential that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

"Syngeneic" refers to deriving from, originating in, or being members of the same species that are genetically identical, particularly with respect to antigens or immunological reactions. These include identical twins having matching MHC types. Thus, a "syngeneic transplant" refers to transfer of cells or organs from a donor to a recipient who is genetically identical to the donor.

"Xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

EXAMPLES

The following examples are simply intended to further illustrate and explain the present invention. The invention, therefore, should not be limited to any of the details in these examples.

Example 1: Expansion of HSCs Ex Vivo in Co-Culture with Bone Marrow Monocytes and Macrophages Isolation of Mouse Bone Marrow Cells (BMCs), Mononuclear Cells (BM-MNCs), Lineage-Negative Hematopoietic Cells (Lin⁻ Cells), and HSC-Enriched LSK Cells.

The femora and tibiae were harvested from mice immediately after they were euthanized with $CO_2$. BM cells were flushed from the bones into HBSS containing 2% FCS using a 21-gauge needle and syringe. Cells from three to ten mice were pooled and centrifuged through Histopaque 1083 (Sigma, St. Louis, Mo.) to isolate BM-MNCs. For the isolation of Lin⁻ cells, BM-MNCs were incubated with biotin-conjugated rat antibodies specific for murine CD3, Mac-1, CD45R/B220, Ter-119, and Gr-1. The labeled mature lymphoid and myeloid cells were depleted twice by incubation with goat anti-rat IgG paramagnetic beads (Dynal Inc, Lake Success, N.Y.) at a bead:cell ratio of approximately 4:1. Cells binding the paramagnetic beads were removed with a magnetic field. The negatively isolated Lin⁻ cells were washed twice with 2% FCS/HBSS and resuspended in complete medium (RPMI1640 medium supplemented with 10% FCS, 2 mM L-glutamine, 10 µM HEPES buffer, and 100 U/ml penicillin and streptomycin) at $1 \times 10^6$ cells/ml. HSC-enriched LSK cells were sorted with an Aria II cell sorter (BD Biosciences, San Jose, Calif.) after Lin⁻ cells were preincubated with anti-CD16/32 antibody to block the Fcγ receptors and then stained with anti-Sca1-PE and c-Kit-APC-Cy7. Dead cells were excluded by gating out the cells stained positive with propidium iodide (PI).

Isolation of Bone Marrow $Gr-1^{high}$ Monocytes ($Gr-1^{hi}$ MCs), $Gr-1^{low}$ Monocytes ($Gr-1^{low}$ MCs), and Macrophages (Mφ).

$Gr-1^{hi}$ MCs (FIG. 1A, I), $Gr-1^{low}$ MCs (FIG. 1B, IV), and macrophages (Mφ) (FIG. 1C, V) were sorted with an Aria II cell sorter after BMCs were stained with anti-Gr-1-PE, CD115-APC, and F4/80-FITC antibodies as shown in FIG. 1.

Figure 1F:
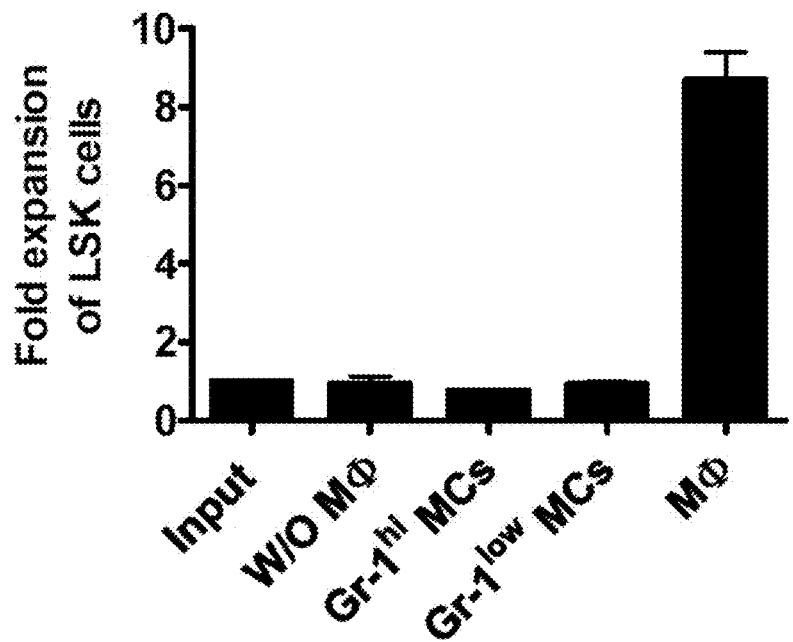

LSK cells ($2 \times 10^3$) were co-cultured with bone marrow $Gr-1^{hi}$ MCs, $Gr-1^{low}$ MCs, and macrophages (Mφ) ($1 \times 10^5$) or cultured alone in a serum free medium supplemented with 20 ng/ml of SCF and TPO for 5 days. The number of total nucleated cells (FIG. 1D) and LSK cells (FIG. 1E) harvested from the cultures were presented as absolute cell counts or fold expansion compared to the input cells. The results show that LSK cells expanded about ~8-fold in co-cultures with macrophages; whereas LSK cells decreased to about 40% of the input in cultures without macrophages. Monocytes had no significant effect on LSK cell expansion (FIG. 1F).

Figure 2A:
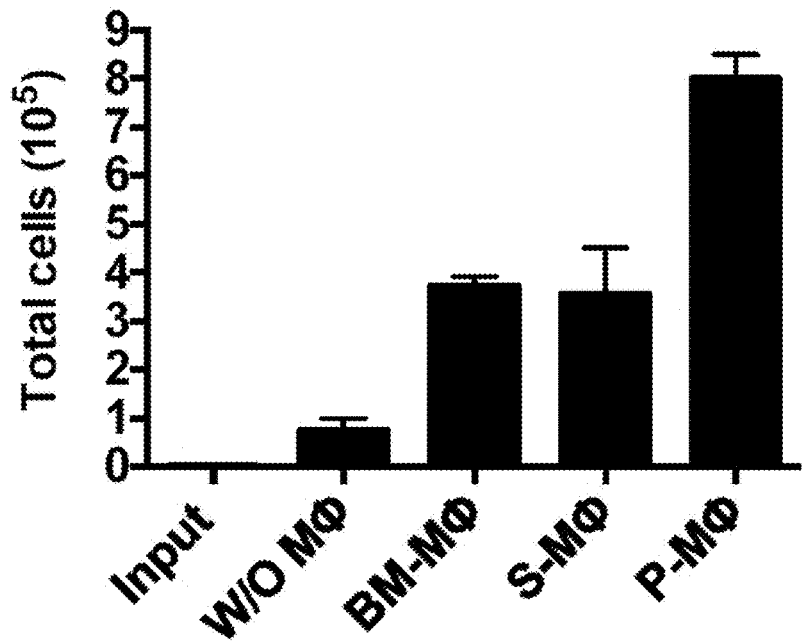
FIG. 2A, FIG. 2B and FIG. 2C show that macrophages isolated from bone marrow (BM-Mφ), spleen (SP-Mφ), and peritoneal cavity (PC-Mφ) can promote LSK cell expansion ex vivo. The number of total cells (FIG. 2A), LSK cells (FIG. 2B) and fold of expansion of LSK cells (FIG. 2C) are graphically depicted for HSC expansion cultures including macrophages isolated from different tissues. Cells without expansion culture (Input) and cultured without macrophages (W/O Mφ) were included as controls.
Figure 2B:
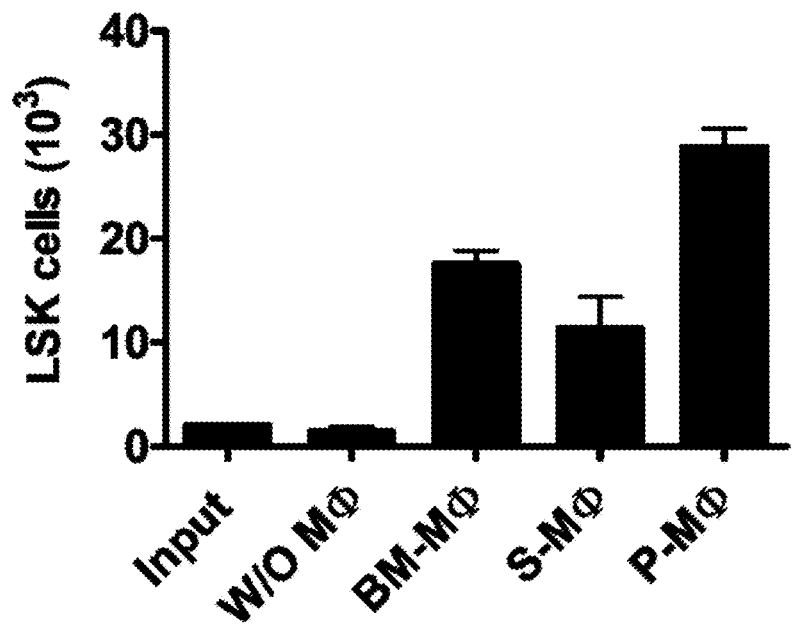
Figure 2C:
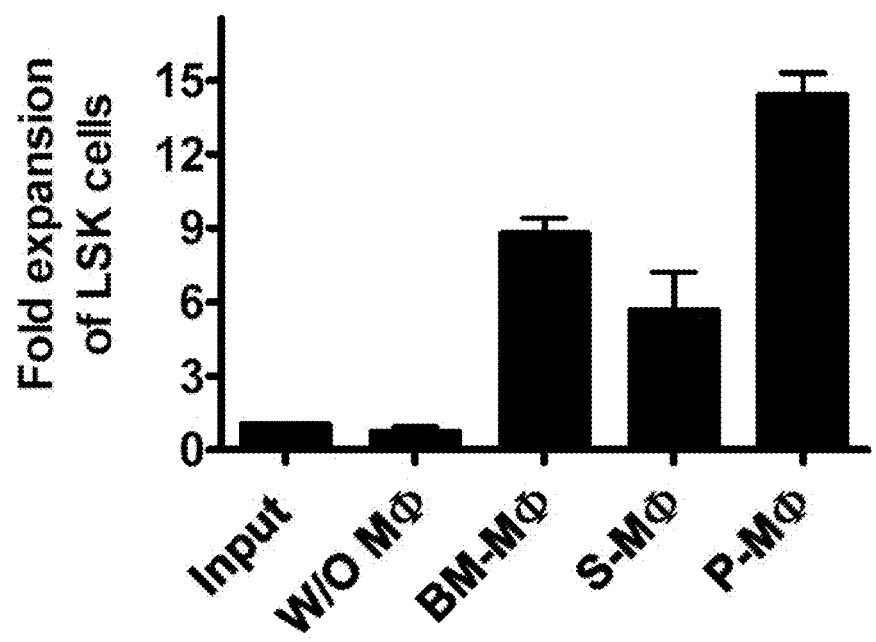

Example 2: Expansion of HSCs Ex Vivo in Co-Culture with Macrophages from Different Tissues LSK cells ($2\times10^3$) were co-cultured with macrophages ($1\times10^5$) from the bone marrow (BM-Mφ), peritoneal cavity (PC-Mφ), and spleen (SP-Mφ) or cultured without macrophages (W/O Mφ) in a serum free medium supplemented with 20 ng/ml of SCF and TPO for 5 days. The number of total nucleated cells (FIG. 2A) and LSK cells (FIG. 2B) harvested from the cultures were presented as absolute cell counts compared to the input cells. The results showed that LSK cells co-cultured with BM-Mφ, SP-Mφ, and PC-Mφ expanded about 8.7-, 5.6-, and 14.4-fold, respectively, whereas the cells cultured without macrophages resulted in about 40% reduction in LSK cells (FIG. 2C).

Figure 3A:
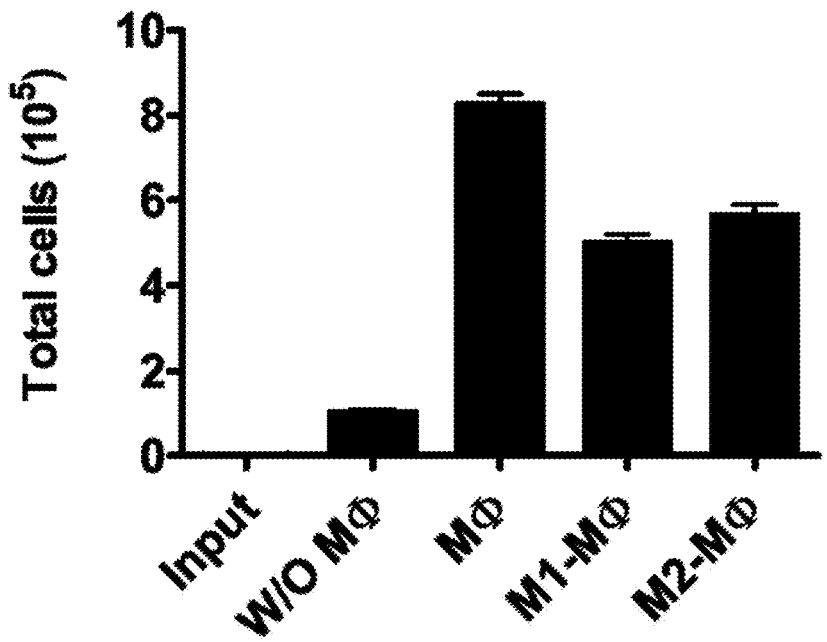
FIG. 3A, FIG. 3B, FIG. 3C, FIG. 3D and FIG. 3E graphically illustrate that M2-polarized macrophages promote and M1-polarized macrophages inhibit ex vivo expansion of HSCs. The number of total cells (FIG. 3A), LSK cells (FIG. 3B), and fold of expansion of LSK cells (FIG. 3C) are graphically depicted for HSC expansion cultures including unpolarized (Mφ), M1 polarized (M1-Mφ), and M2 polarized (M2-Mφ) macrophages.
Figure 3B:
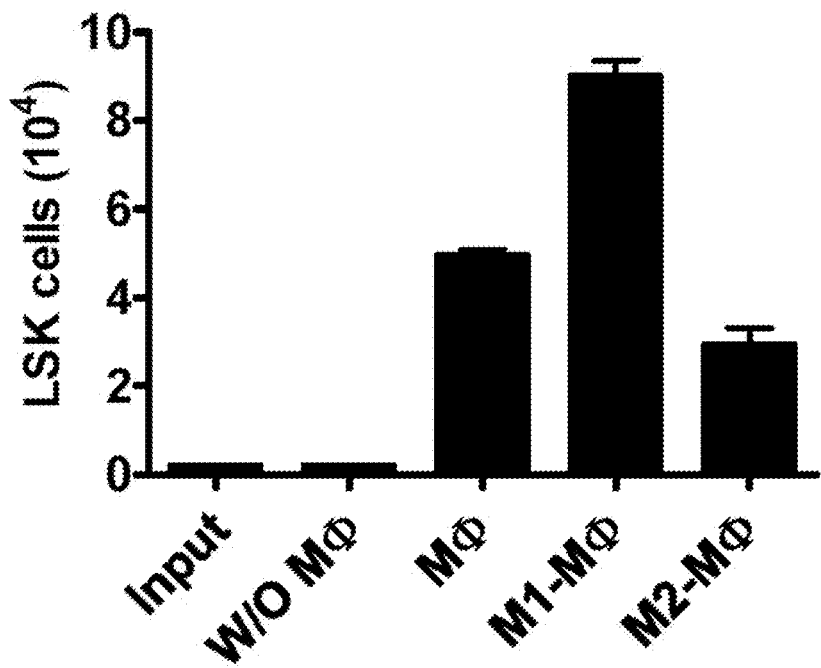
Figure 3C:
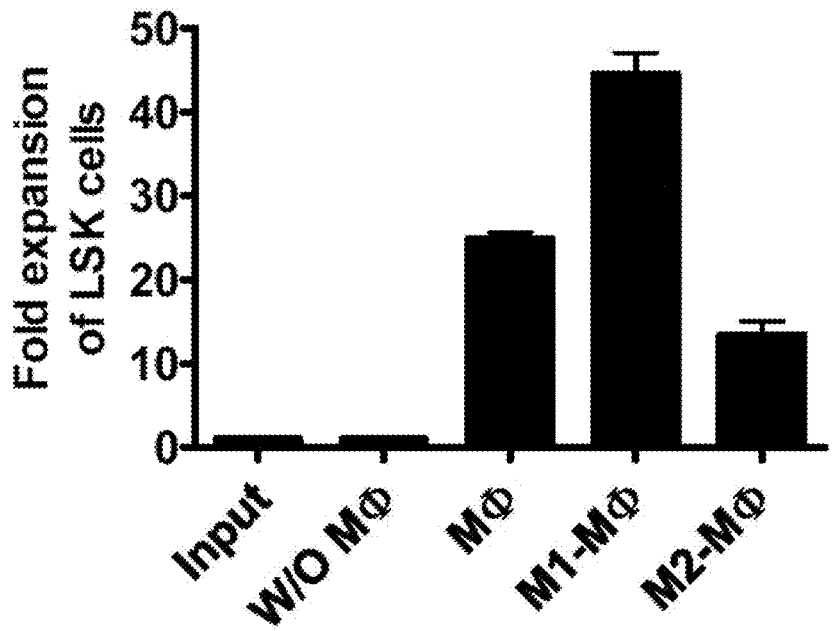
Figure 3D:
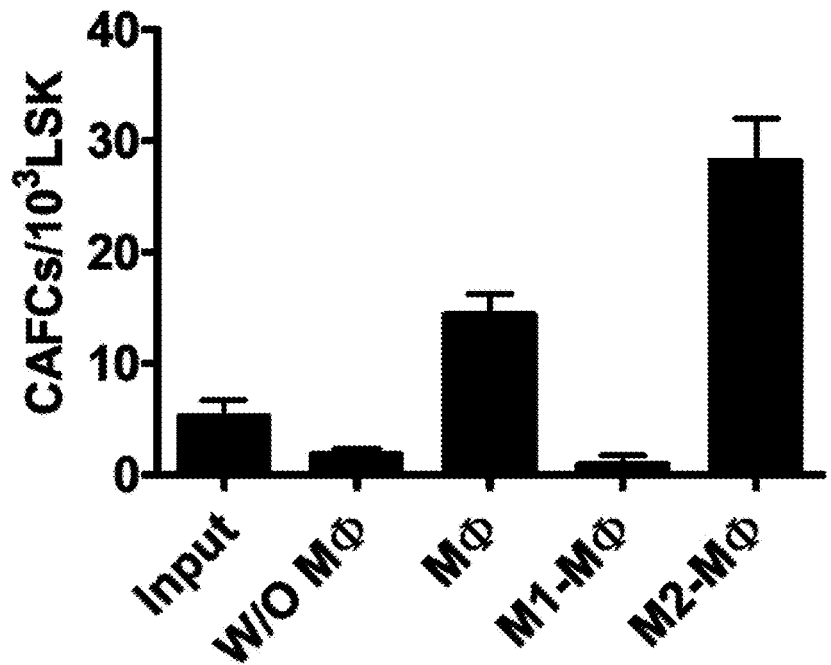
Figure 3E:
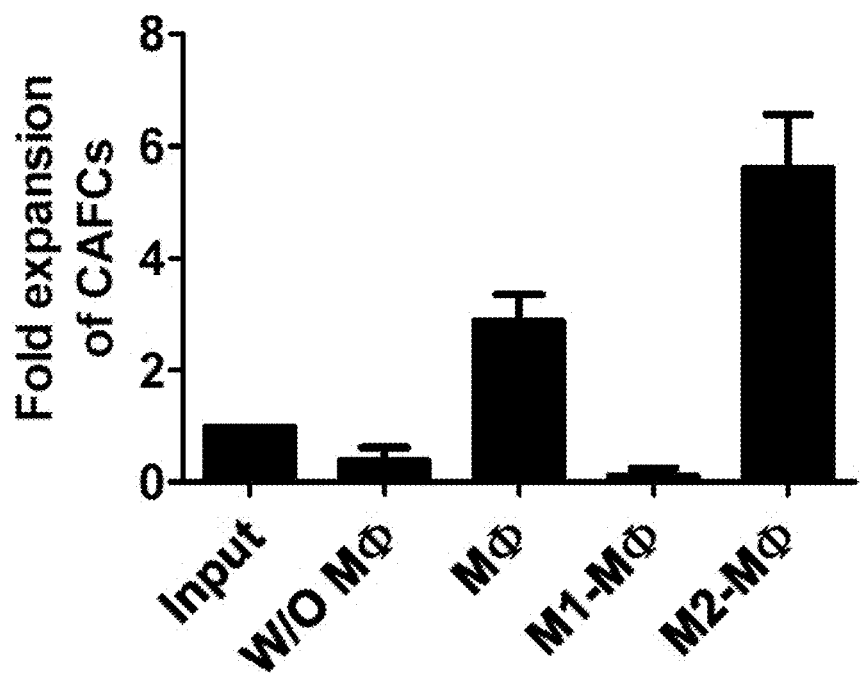

Example 3: M2 but not M1 Polarized Macrophages Promote HSC Ex Vivo Expansion Macrophages were isolated from mouse peritoneal cavity. They were polarized to M1 (M1-Mφ) and M2 macrophages (M2-Mφ) by incubation with IFN-γ (40 ng/ml) and IL-4 (40 ng/ml) overnight, respectively. Macrophages incubated with vehicle (PBS) overnight were included as unpolarized control macrophages (Mφ). LSK cells ($2\times10^3$) were co-cultured with $1\times10^5$ M1-Mφ, M2-Mφ or Mφ or without Mφ (W/O Mφ) as described in Example 2 above. After 5 days of incubation, cells were collected from the cultures and analyzed. The number of total nucleated cells (FIG. 3A) and LSK cells (FIG. 3B) harvested from the cultures were presented as absolute cell counts. The fold expansion of LSK cells were presented in FIG. 3C in comparison with the input cells. The expansion of HSCs was measured by 5-week CAFC assay (FIG. 3D,E). The results show that M2-Mφ were more effective in promoting ex vivo expansion of HSCs according to the CAFC assay than unpolarized macrophages (Mφ) (FIG. 3D,E), even though they were less effective in promoting the expansion of total cells and LSK cells (FIG. 3A-C). In contrast, M1-Mφ inhibited HSC expansion because LSK cells co-cultured with M1-Mφ showed a significant reduction in the number of 5-week CAFCs (FIG. 3D,E).

Figure 4A:
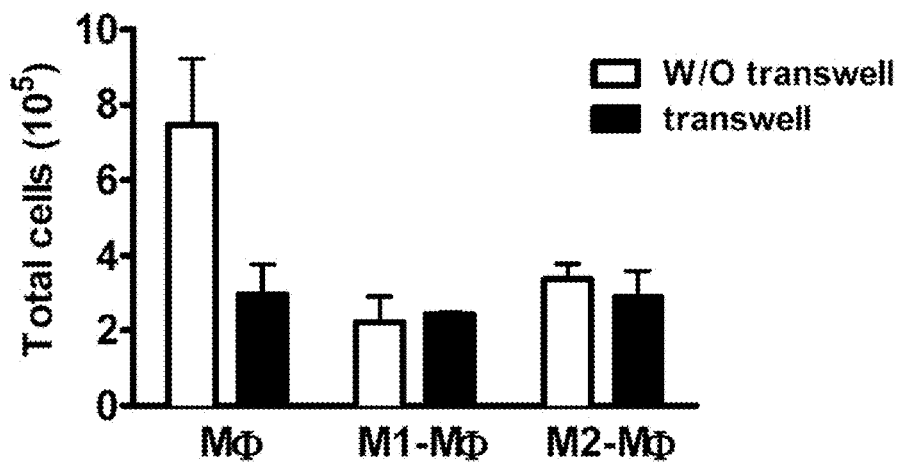
FIG. 4A, FIG. 4B, FIG. 4C, FIG. 4D, and FIG. 4E graphically illustrate the effect of macrophages on HSC ex vivo expansion with or without direct contact. The number of total cells (FIG. 4A), LSK cells (FIG. 4B), fold of expansion of LSK cells (FIG. 4C), CAFCs of the expanded cells (FIG. 4D) and fold of expansion of CAFCs (FIG. 4E) are graphically depicted for co-cultures of HSCs with macrophages (M1-polarized, M2-polarized or not polarized) in a transwell (+) to avoid cell-cell contact or a regular culture plate (−) which allows direct cell-cell interaction and without macrophages (W/O Mφ). Cells without expansion culture (Input) were included as a control.
Figure 4B:
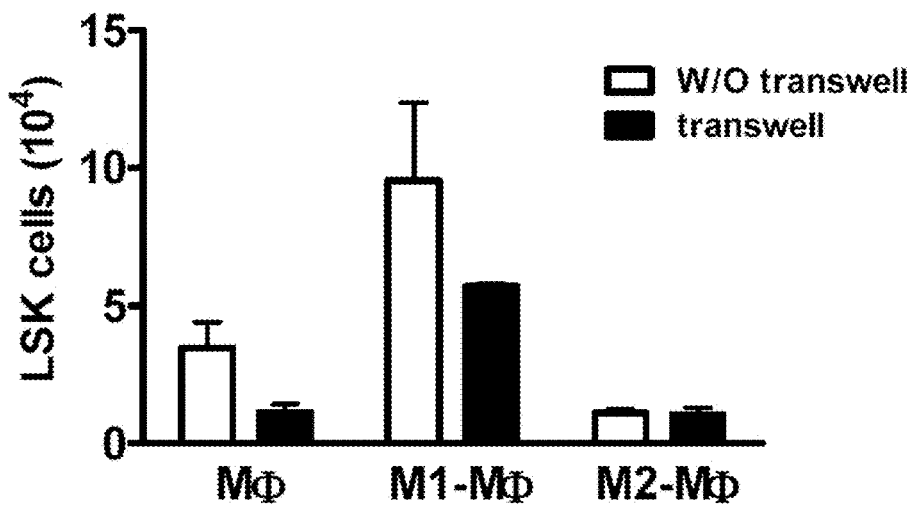
Figure 4C:
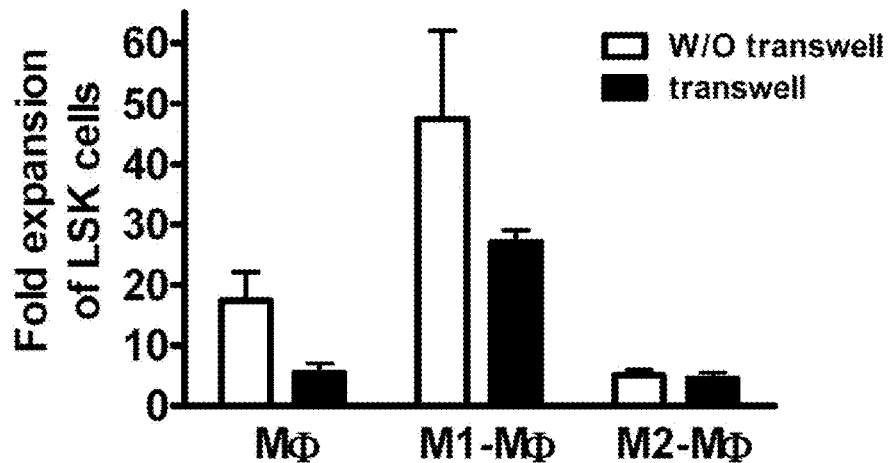
Figure 4D:
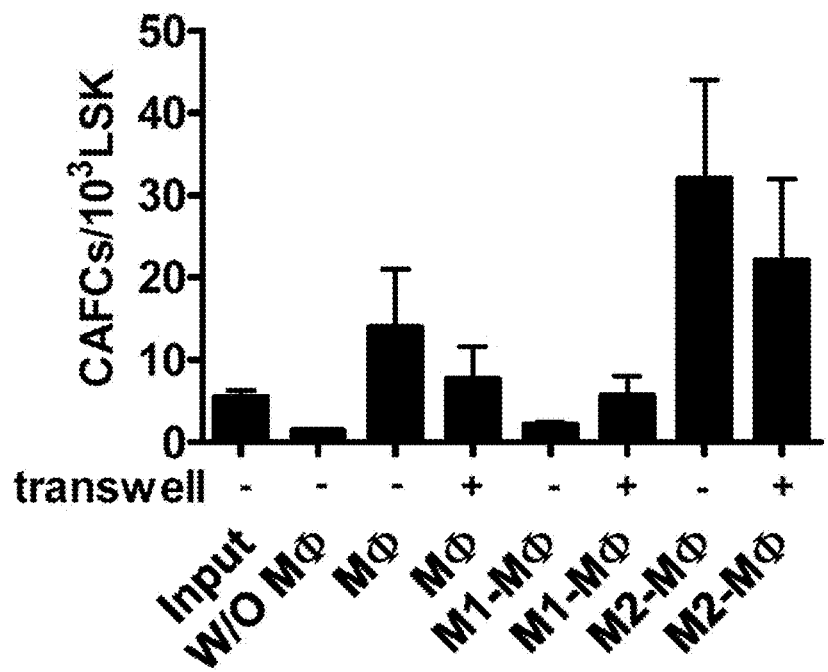
Figure 4E:
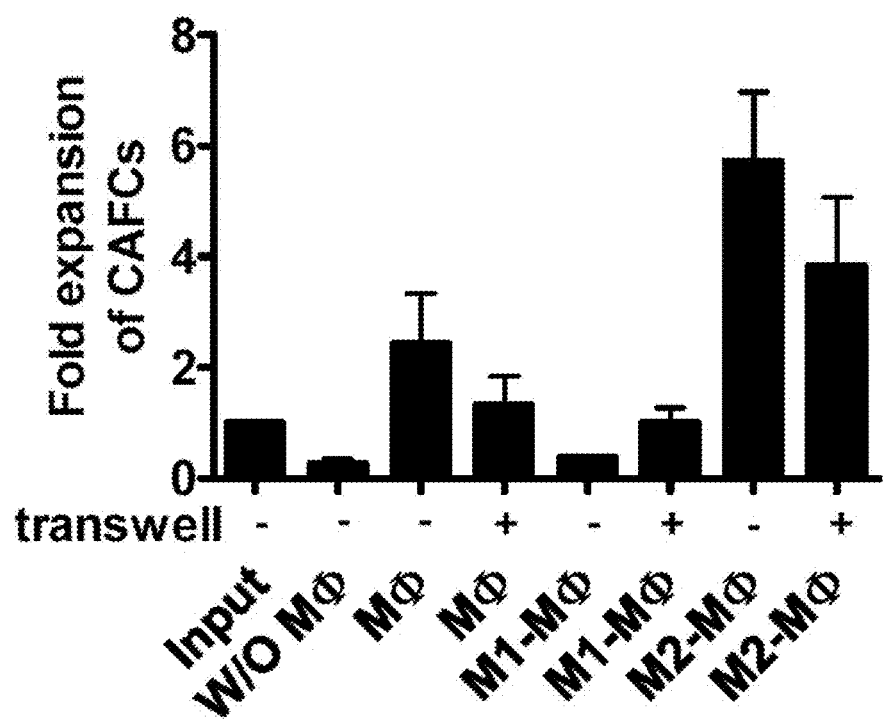
Figure 5A:
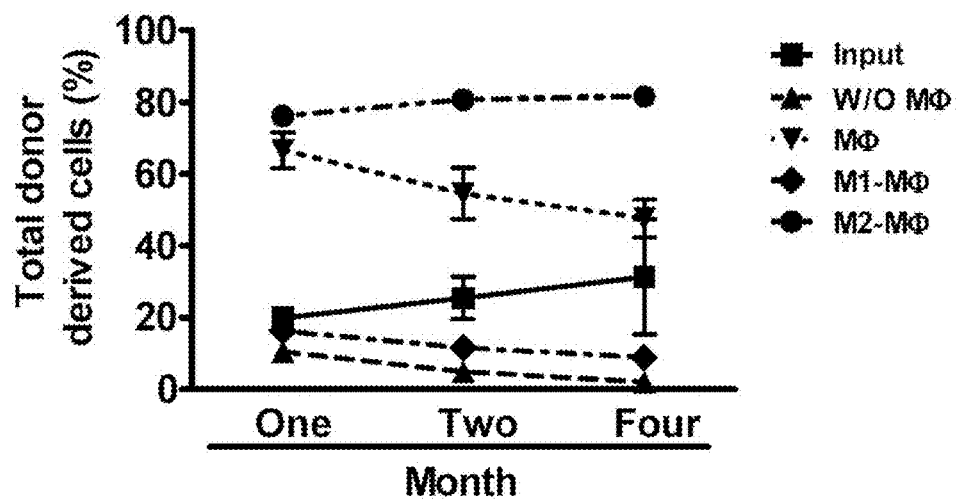
FIG. 5A, FIG. 5B, FIG. 5C, FIG. 5D, FIG. 5E, FIG. 5F, FIG. 5G and FIG. 5H graphically illustrate the engraftment ability of LSK cells cultured with macrophages (Mφ) or M2 polarized macrophages (M2-Mφ) increases significantly after transplanted into lethality irradiated recipients compared to freshly isolated HSC cells (Input), whereas the engraftment ability of the cells cultured without macrophages (W/O Mφ) or with M1 polarized macrophages (M1-Mφ) was reduced (FIG. 5A) after transplantation. The engraftment of T lymphocytes (T cells.
Figure 5B:
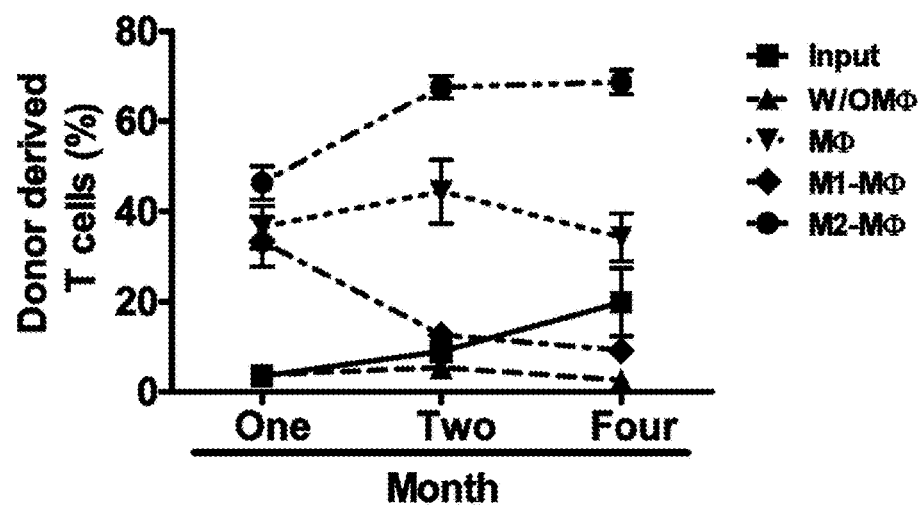
Figure 5C:
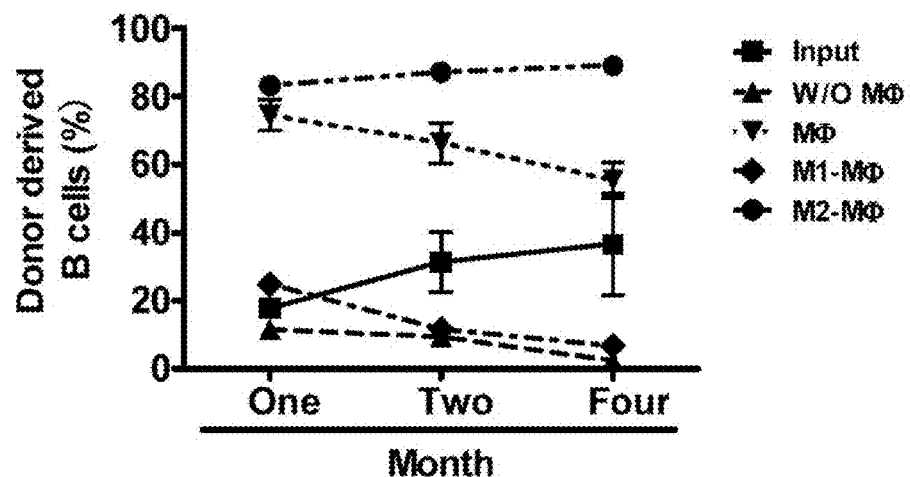
Figure 5D:
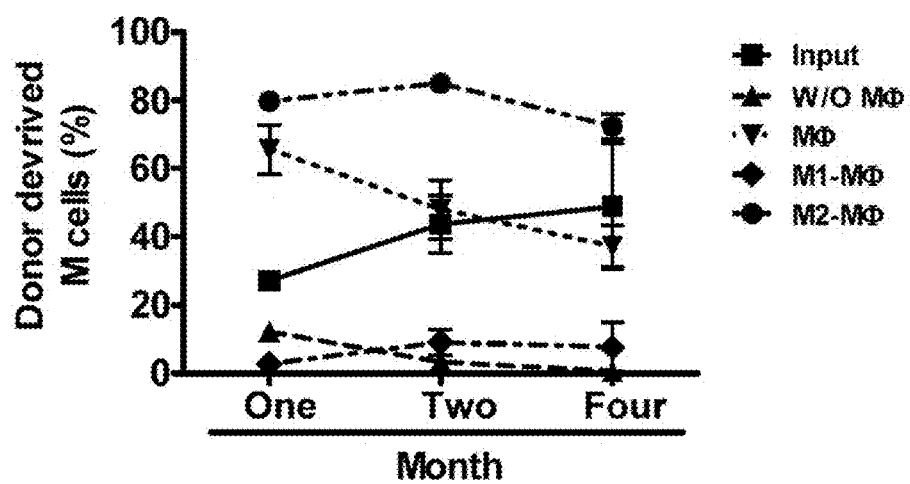
Figure 5E:
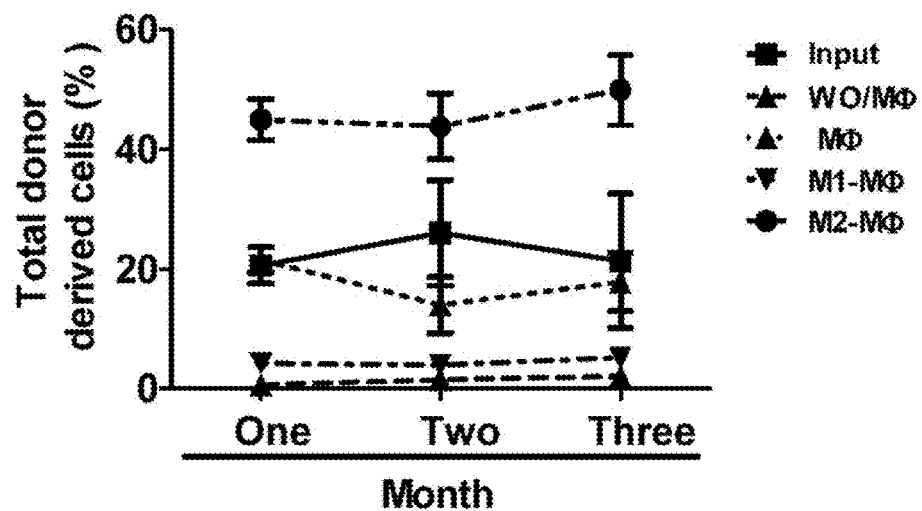
Figure 5F:
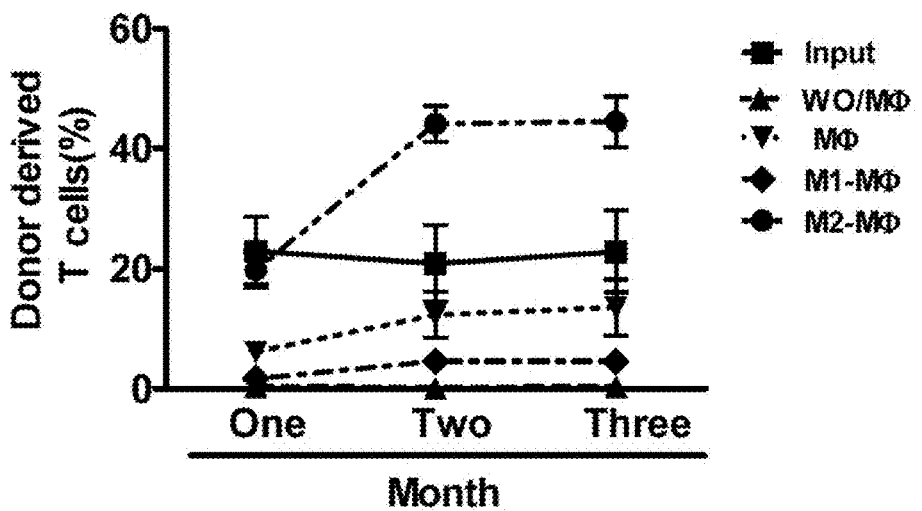
Figure 5G:
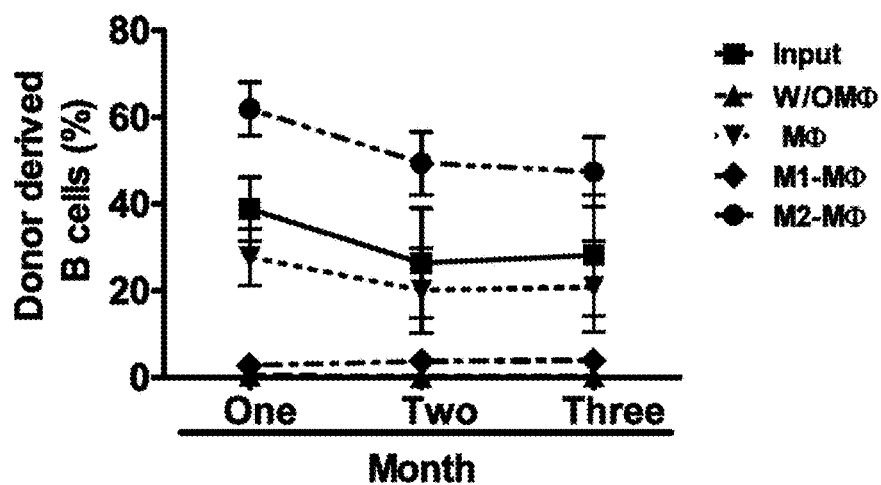
Figure 5H:
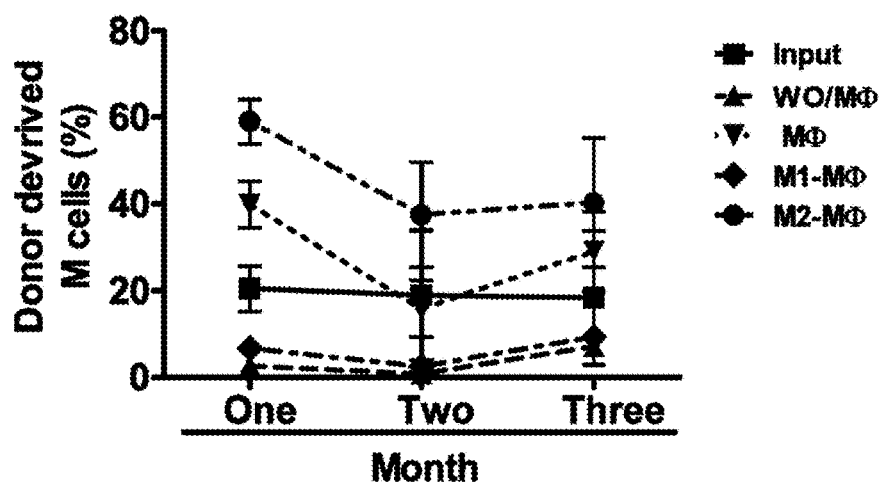

Example 4: Both a Direct Contact with Macrophages and Soluble Factors Secreted by Macrophages are Required to Promote In Vitro Expansion of HSC Cells Macrophages were isolated from mouse peritoneal cavity and polarized as described above. LSK cells ($2\times10^3$) were co-cultured with $1\times10^5$ peritoneal M1 (M1-Mφ) or M2 macrophages (M2-Mφ) in a transwell plate (+) to avoid cell-cell direct contact or in a regular culture plate (−) which allows direct cell-cell interaction or without macrophages (W/O Mφ) in a serum free medium supplemented with 20 ng/ml of SCF and TPO for 5 days. The number of total nucleated cells (FIG. 4A) and LSK cells (FIG. 4B) harvested from the cultures were presented as absolute cell counts (FIG. 4A,B). The fold expansion of LSK cells were presented in FIG. 4C in comparison with the input cells. The results showed that macrophages can promote LSK cell expansion via cell-cell contact and macrophage-derived soluble factors (FIG. 4). In addition, greater fold expansions of HSCs were observed when LSK cells were co-cultured with unpolorazed macrophages (Mφ) and M2-Mφ in a non-transwell culture than in a transwell culture, whereas the expansion of HSCs were suppressed less by M1-Mφ in a transwell culture than in a non-transwell culture, according to the CAFC assay (FIG. 4D,E).

Example 5: Effects of Mφ, M1-Mφ and M2-Mφ on HSC Engraftment

Macrophages were isolated from mouse peritoneal cavity and polarized; and LSK cells ($2\times10^3$, from C57BL/6-CD45.2 mice) were co-cultured with $1\times10^5$ M1-Mφ, M2-Mφ or unpolarized macrophages (Mφ) or without macrophages (W/O Mφ), as described above. After 5 days of expansion, cells were collected from all of these cultures. The expanded cells and $2\times10^3$ unexpanded LSK cells (Input) were injected into lethal irradiated recipients (C57BL/6-CD45.1 mice) along with $2\times10^5$ competitive bone marrow cells from C57BL/6-CD45.1 mice (n=5-6 mice/group). One, two, and four months after transplantation, the peripheral blood was collected from each recipient. They were analyzed by flow cytometry for donor cell engraftment after red blood cells were lysed and the cells were stained with FITC-conjugated anti-mouse CD45.2, APC-conjugated anti-mouse Thy1.2, APC- and PE-conjugated anti-mouse B220, and PE-conjugated anti-mouse GR-1 and CD11b antibodies. Percentages of total donor-derived white blood cells, and donor-derived T, B, and myeloid (M) cells are presented in FIG. 5A-D. In addition, the primary recipients were sacrificed four months after transplantation to harvest bone marrow cells. One million of these bone marrow cells were then injected into lethally irradiated secondary recipients (C57BL/6-CD45.1). One, two, and three months after the secondary transplantation, the peripheral blood was collected and analyzed for donor cell engraftment as described above by flow cytometry. Percentages of total donor-derived white blood cells, and donor-derived T, B, and myeloid (M) cells in the secondary recipients are presented in FIG. 5E-H.

Figure 6A:
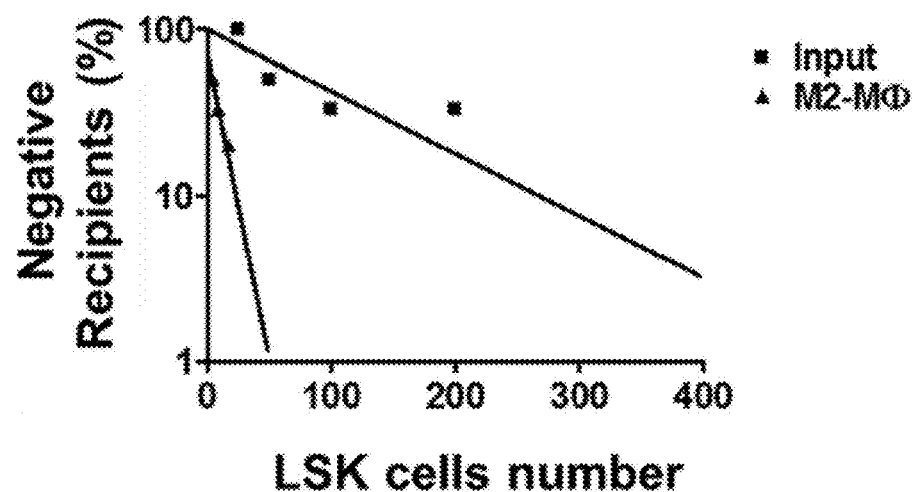
FIG. 6A and FIG. 6B graphically illustrate that the frequency of competitive repopulating units (CRU) was dramatically increased after being co-cultured with M2-Mφ. The short term CRU (two months) frequency of input cells is 1/133, while the short term CRU frequency of co-cultured cells is 1/7.87 (FIG. 6A). The long term CRU (four months) frequency of input cells is 1/293, while the long term CRU frequency of co-cultured cells is 1/22.7 (FIG. 6B).
Figure 6B:
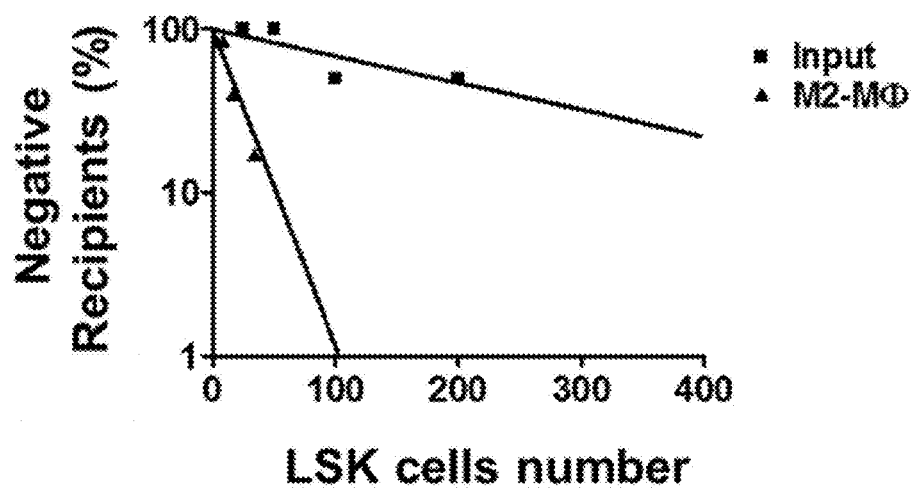

Example 6: M2-Mφ Increases the Competitive Repopulating Units (CRUS) of HSCs after Ex Vivo Expansion Lethally irradiated congenic (C57BL/6-CD45.1) recipient mice (n=6) were reconstituted with 25, 50, 100, or 200 LSK cells freshly isolated from C57BL/6-CD45.2 mice or the progeny of 4.2, 8.5, 17, or 34 CD45.2 LSK cells harvested from a 10-day co-culture with M2-Mφ as described above along with 200,000 whole bone marrow cells from C57BL/6-CD45.1 mice. Peripheral blood donor cell engraftments in the recipients were analyzed as described above by flow cytometry. If the percentage of donor-derived cells in the blood from a recipient is less than 1% and/or fails to show multilineage differentiation, the transplant is considered negative for engraftment. The data is presented as percentage of negative engraftment in FIG. 6A,B. Calculation of CRU according to poisson distribution demonstrates that co-culture with M2-Mφ increased short term CRUs from 1/133 LSK to 1/7.8 LSK, and long term CRUs from 1/293 LSK to 1/22.7 LSK, representing 17- and 13-fold expansion, respectively.

Figure 7A:
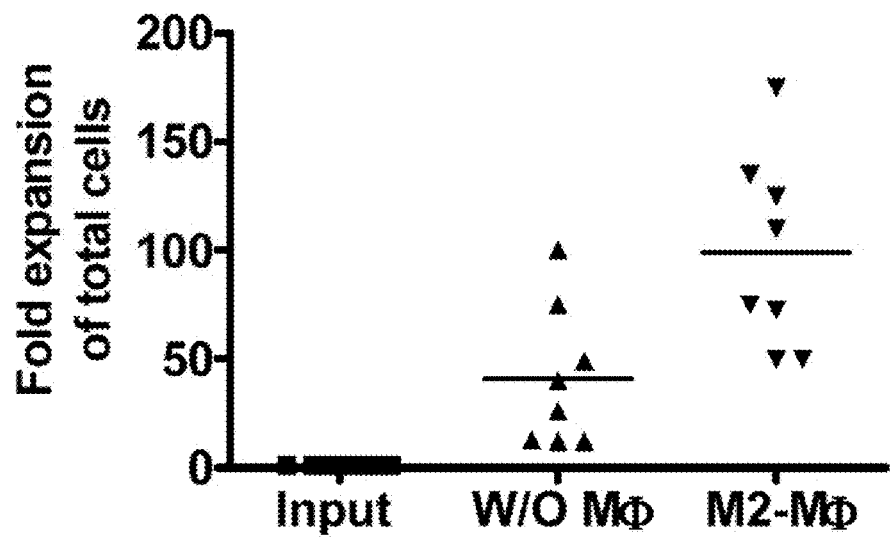
FIG. 7A, FIG. 7B, FIG. 7C and FIG. 7D graphically illustrate that human M2 polarized macrophages induce human cord blood CD34$^+$ cells expansion in vitro. Fold expansion of total cells (FIG. 7A), fold of expansion of CD34$^+$ cells (FIG. 7B), CAFCs of the expanded cells (FIG. 7C) and fold of expansion of CAFCs (FIG. 7D) are graphically depicted for co-cultures of CD34$^+$ cells with M2 polarized macrophages. Cells cultured without macrophages (W/O Mφ) were included as a control.
Figure 7B:
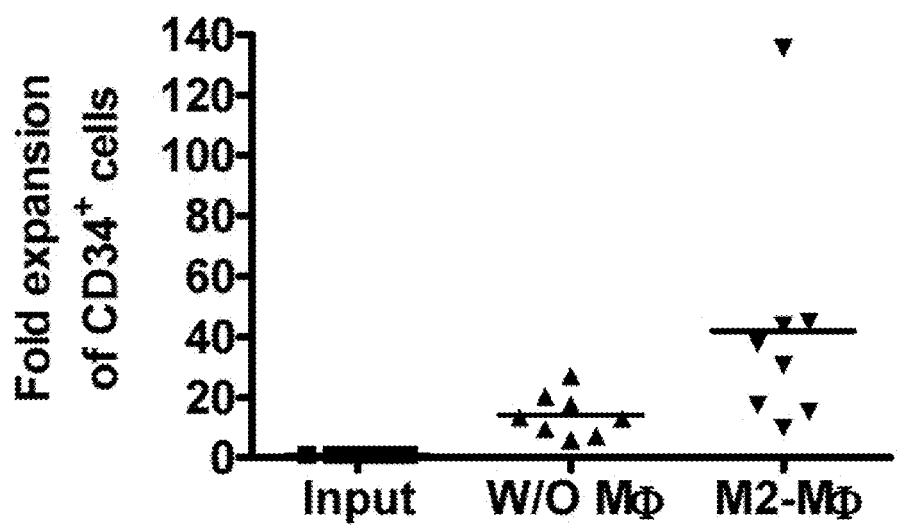
Figure 7C:
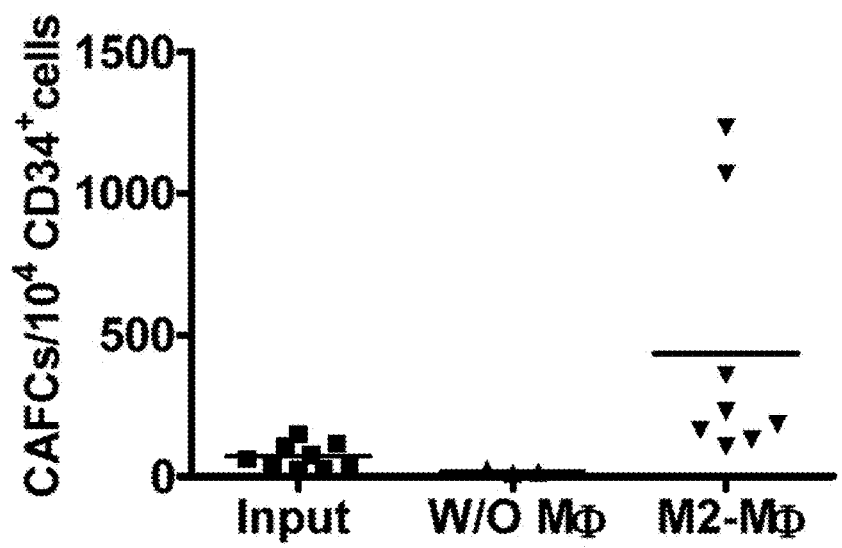
Figure 7D:
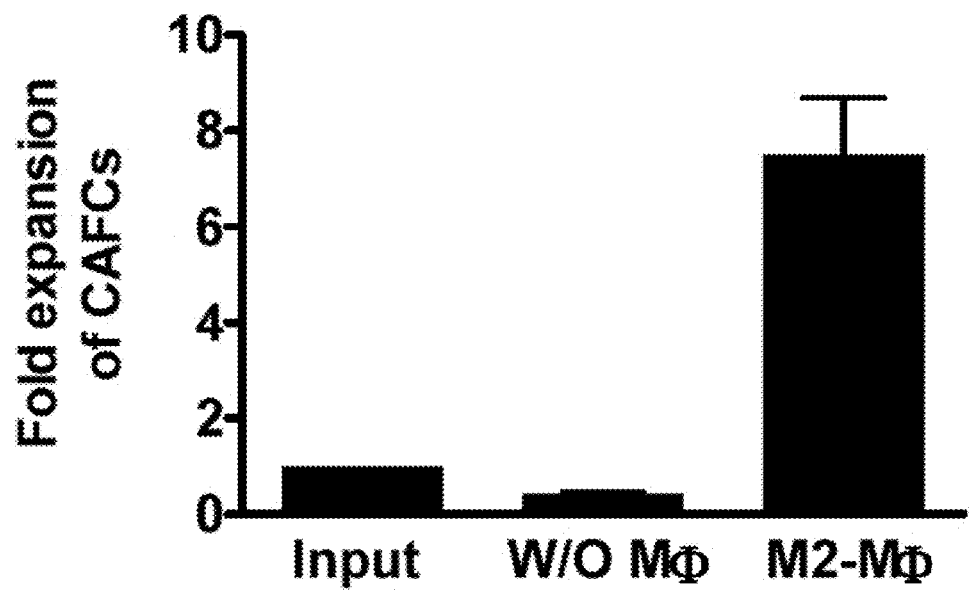

Example 7: Co-Culture with M2-Mφ Promotes Ex Vivo Expansion of Human Cord Blood HSC/HPCs Cord blood units were collected from cord blood cells bank of University of Arkansas For Medical Sciences. Cord blood mononuclear cells (CB-MNCs) were isolated by Ficoll-Hypaque density centrifugation, and CD34⁺ and CD34⁻ cells were isolated by an immunomagnetic selection kit (Myltenyi) according to the manufacturer's instructions. They were stored in liquid nitrogen in a frozen medium (DMEM+20% FBS+10% Dimethyl sulfoxide) until being used. After thawing quickly and washed once with PBS, CD34⁻ cells (2×10$^6$ per well) were differentiated to macrophages in a 12 well plate with a macrophage differentiation culture medium (DMEM+20% FBS+50 ng/ml hSCF+50 ng/ml hM-CSF) for 7 days. On day 8, 40 ng/ml hIL-4 was added to the culture to polarize the differentiated macrophages into M2-Mφ overnight. On day 9, thawed CD34⁺ cells (1×10$^4$ per well) were seeded to the plate and cultured in human HSC expansion medium (a serum free medium+ hSCF 50 ng/ml+hFlt-3 ligand 50 ng/ml+hTPO 50 ng/ml). Meanwhile, the same number of CD34+ cells was cultured in human HSC expansion medium without macrophages as control (W/O Mφ). After 7 days of expansion, the suspension cells were harvested from the culture to numerate the total number of nucleated cells and analyze the frequencies of CD34+ cells by flow cytometry after immunostaining with APC-conjugated anti-human CD34 antibody. The fold expansion of total nucleated cells and CD34+ cells was calculated and presented in FIGS. 7A and 7B, respectively, in comparison with input CD34+ cells. In addition, fold expansion of HSCs was calculated according to the numbers of week-6 CAFCs in input CD34+ cells and the progeny from expanded CD34+ cells co-cultured with M2-Mφ or without macrophages (W/O Mφ) as shown in FIG. 7C,D.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

What is claimed is:

1. A method of expanding an isolated population of hematopoietic stem cells (HSCs) comprising:
    a) culturing a starter cell population of HSCs;
    b) adding M2 polarized macrophages and optionally at least one macrophage-derived secretion factor to the starter cell population to form an expanding HSC population; and,
    c) culturing the expanding HSC population to form an expanded HSC population, wherein the number of long term expanded HSCs is increased in comparison to the number of long term HSCs in the starter cell population, wherein the HSCs have improved expansion and engraftment capabilities compared to HSCs expanded with non-polarized macrophages.

2. The method of claim 1, further comprising adding additional factors to the starter cell population.

3. The method of claim 2, wherein the additional factors are selected from the group consisting of cytokines, growth factors, proteins, polypeptides, small molecules, nutrients, expression vectors, and combinations thereof.

* * * * *